(12) United States Patent
Shokat et al.

(10) Patent No.: US 9,512,125 B2
(45) Date of Patent: Dec. 6, 2016

(54) SUBSTITUTED PYRAZOLO[3,4-D] PYRIMIDINES AS ANTI-INFLAMMATORY AGENTS

(75) Inventors: Kevan M. Shokat, San Francisco, CA (US); Nikolai Sepetov, Los Gatos, CA (US); Chao Zhang, San Francisco, CA (US); Heinz W. Gschwend, Santa Rosa, CA (US); Eric J. Kunkel, San Mateo, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1697 days.

(21) Appl. No.: 11/719,722

(22) PCT Filed: Nov. 21, 2005

(86) PCT No.: PCT/US2005/042524
§ 371 (c)(1),
(2), (4) Date: Dec. 5, 2008

(87) PCT Pub. No.: WO2006/068760
PCT Pub. Date: Jun. 29, 2006

(65) Prior Publication Data
US 2009/0124638 A1    May 14, 2009

Related U.S. Application Data

(60) Provisional application No. 60/629,639, filed on Nov. 19, 2004.

(51) Int. Cl.
| | | |
|---|---|---|
| C07D 487/04 | (2006.01) |
| A61K 31/519 | (2006.01) |
| A61P 29/00 | (2006.01) |
| A61P 35/00 | (2006.01) |
| A61P 9/00 | (2006.01) |
| A61P 19/02 | (2006.01) |
| A61P 25/28 | (2006.01) |
| A61P 25/16 | (2006.01) |
| A61P 25/22 | (2006.01) |
| A61P 25/24 | (2006.01) |
| A61P 9/10 | (2006.01) |

(52) U.S. Cl.
CPC .................................. C07D 487/04 (2013.01)

(58) Field of Classification Search
CPC ................................................... C07D 487/04
USPC ....................................... 544/262; 514/262.1
See application file for complete search history.

(56) References Cited

U.S. PATENT DOCUMENTS

| | | |
|---|---|---|
| 4,704,381 A | 11/1987 | Schaumann et al. |
| 4,861,760 A | 8/1989 | Mazuel et al. |
| 4,911,920 A | 3/1990 | Jani et al. |
| 5,212,162 A | 5/1993 | Missel et al. |
| 5,240,941 A | 8/1993 | Bruneau |
| 5,310,731 A | 5/1994 | Olsson et al. |
| 5,364,862 A | 11/1994 | Spada et al. |
| 5,403,841 A | 4/1995 | Lang et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |

(Continued)

FOREIGN PATENT DOCUMENTS

| | | |
|---|---|---|
| CA | 1338379 | 6/1996 |
| CN | 101602768 | 12/2009 |

(Continued)

OTHER PUBLICATIONS

Kreutzberger et. al. (Justus Liebigs Annalen der Chemie, 1977, (4), pp. 537-544).*
Bhat, G. A., et al., "Pyrazolopyrimidine nucleosides. 12. Synthesis and biological activity of certain pyrazolo[3,4-d]pyrimidine nucleosides related to adenosine," J. Med. Chem. vol. 24, No. 10, (1981), pp. 1165-1172.
Pietrie et al., "novel biotinylated adenylate analogue derived from pyrazolo[3,4-d]pyrimidine for labeling DNA probes," Bioconj. Chem. vol. 2, No. 6, (1991), pp. 441-446.
Examination Report for GB Application No. GB0819947.3 dated Oct. 27, 2010, 2 pages.

(Continued)

*Primary Examiner* — Susanna Moore
(74) *Attorney, Agent, or Firm* — Mintz Levin Cohn Ferris Glovsky and Popeo, P.C.

(57) ABSTRACT

The present invention provides anti-inflammatory compounds useful in the treatment of diseases and conditions in which inflammation is involved in disease progression or the manifestation of symptoms of the disease or condition.

6 Claims, 3 Drawing Sheets

(56) References Cited

U.S. PATENT DOCUMENTS

| | | |
|---|---|---|
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhaesebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 * | 5/2009 | Arnold et al. ........... 514/255.05 |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 8,642,604 B2 | 2/2014 | Knight et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 * | 4/2003 | Shokat ...................... 435/184 |
| 2003/0083268 A1 | 5/2003 | Burli et al. |
| 2003/0109248 A1 | 6/2003 | Lewis |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer, Jr. et al. |
| 2003/0166929 A1 | 9/2003 | Snow et al. |
| 2003/0180924 A1 | 9/2003 | Desimone et al. |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |

(56) References Cited

U.S. PATENT DOCUMENTS

| | | |
|---|---|---|
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Milian et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0325967 A1 | 12/2009 | Fairhurst et al. |
| 2010/0009963 A1 | 1/2010 | Knight et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0065154 A1 | 3/2012 | Tanaka et al. |
| 2012/0294930 A1 | 11/2012 | Ren et al. |
| 2012/0322814 A1 | 12/2012 | Korennykh et al. |
| 2014/0066462 A1 | 3/2014 | Pearce et al. |
| 2015/0031881 A1 | 1/2015 | Tanaka et al. |

FOREIGN PATENT DOCUMENTS

| | | |
|---|---|---|
| EP | 0 496 617 A1 | 7/1992 |
| EP | 0 496 617 B1 | 7/1992 |
| EP | 773023 A1 | 5/1997 |
| EP | 1020445 B1 | 8/2008 |
| GB | 812366 | 4/1959 |
| GB | 937725 | 9/1963 |
| JP | 61109797 | 5/1986 |
| JP | 05-112595 A | 5/1993 |
| JP | 5256693 | 10/1993 |
| JP | 8295667 A | 11/1996 |
| JP | 9143163 A | 6/1997 |
| JP | 10206995 A | 8/1998 |
| JP | 11-502859 A | 3/1999 |
| JP | 11-507390 A | 6/1999 |
| JP | 2000072773 A | 3/2000 |
| JP | 2002-037787 A | 2/2002 |
| JP | 2002131859 A2 | 5/2002 |
| JP | 2003073357 A2 | 3/2003 |
| JP | 2004161716 A | 6/2004 |
| WO | WO83/01446 A1 | 4/1983 |
| WO | WO91/17161 A1 | 11/1991 |
| WO | WO92/14733 A1 | 9/1992 |
| WO | WO93/16091 A1 | 8/1993 |
| WO | WO93/16092 A1 | 8/1993 |
| WO | WO93/18035 A1 | 9/1993 |
| WO | WO93/22443 A1 | 11/1993 |
| WO | WO 94/13677 | 6/1994 |
| WO | WO 94/17803 | 8/1994 |
| WO | WO95/12588 A1 | 5/1995 |
| WO | WO95/29673 A1 | 11/1995 |
| WO | WO95/32984 A1 | 12/1995 |
| WO | WO-96/31510 A1 | 10/1996 |
| WO | WO 96/40706 A1 | 12/1996 |
| WO | WO-96/40706 A1 | 12/1996 |
| WO | WO 97/15658 A1 | 5/1997 |
| WO | WO97/28133 A1 | 8/1997 |
| WO | WO97/28161 A1 | 8/1997 |
| WO | WO98/41525 A1 | 9/1998 |
| WO | WO98/52611 A1 | 11/1998 |
| WO | WO98/57952 A1 | 12/1998 |
| WO | WO00/17202 A1 | 3/2000 |

(56) References Cited

FOREIGN PATENT DOCUMENTS

| | | |
|---|---|---|
| WO | WO01/02369 A2 | 1/2001 |
| WO | 01/19829 A2 | 3/2001 |
| WO | WO01/16114 A2 | 3/2001 |
| WO | WO01/19829 A2 | 3/2001 |
| WO | WO01/25238 A2 | 4/2001 |
| WO | WO01/31063 A1 | 5/2001 |
| WO | WO01/38584 A2 | 5/2001 |
| WO | WO01/16114 A3 | 8/2001 |
| WO | WO01/55140 A1 | 8/2001 |
| WO | WO01/56988 A1 | 8/2001 |
| WO | WO01/19829 A3 | 9/2001 |
| WO | WO01/25238 A3 | 10/2001 |
| WO | WO01/38584 A3 | 10/2001 |
| WO | WO01/81346 A2 | 11/2001 |
| WO | WO02/06192 A1 | 1/2002 |
| WO | WO01/81346 A3 | 3/2002 |
| WO | WO01/02369 A3 | 4/2002 |
| WO | WO02/30944 A2 | 4/2002 |
| WO | WO02/057425 A2 | 7/2002 |
| WO | WO 02/076986 A1 | 10/2002 |
| WO | WO02/080926 A1 | 10/2002 |
| WO | WO02/083143 A1 | 10/2002 |
| WO | WO02/088025 A1 | 11/2002 |
| WO | WO02/090334 A1 | 11/2002 |
| WO | WO02/30944 A3 | 1/2003 |
| WO | WO 03/000187 | 1/2003 |
| WO | WO/03/016275 A1 | 2/2003 |
| WO | WO03/020880 A2 | 3/2003 |
| WO | WO03/024969 A1 | 3/2003 |
| WO | WO03/035075 A1 | 5/2003 |
| WO | WO03/059884 A1 | 7/2003 |
| WO | WO03/020880 A3 | 10/2003 |
| WO | WO03/082341 A1 | 10/2003 |
| WO | WO03/106426 A1 | 12/2003 |
| WO | WO2004/006906 A2 | 1/2004 |
| WO | WO2004/006906 A3 | 3/2004 |
| WO | WO2004/018058 A2 | 3/2004 |
| WO | WO2004/031177 A1 | 4/2004 |
| WO | WO2004/039774 A2 | 5/2004 |
| WO | WO2004/018058 A3 | 7/2004 |
| WO | WO2004/039774 A3 | 7/2004 |
| WO | WO03/000187 A3 | 8/2004 |
| WO | WO2004/087053 A2 | 10/2004 |
| WO | WO2004/111014 A1 | 12/2004 |
| WO | WO2005/002585 A1 | 1/2005 |
| WO | WO2005/007085 A | 1/2005 |
| WO | WO2005/012323 A2 | 2/2005 |
| WO | WO2005/016348 A1 | 2/2005 |
| WO | WO2005/016349 A1 | 2/2005 |
| WO | WO2005/016528 A2 | 2/2005 |
| WO | WO2005/021533 A1 | 3/2005 |
| WO | WO02/57425 A3 | 4/2005 |
| WO | WO2005/012323 A3 | 5/2005 |
| WO | WO2005/016528 A3 | 5/2005 |
| WO | WO2005/044181 A2 | 5/2005 |
| WO | WO 2005/047289 | 5/2005 |
| WO | WO2005/061460 A1 | 7/2005 |
| WO | WO2005/063258 A1 | 7/2005 |
| WO | WO2005/067901 A2 | 7/2005 |
| WO | WO2005/074603 A2 | 8/2005 |
| WO | WO2005/007085 A3 | 9/2005 |
| WO | WO2005/097800 A1 | 10/2005 |
| WO | WO2005/105760 A1 | 11/2005 |
| WO | WO2005/067901 A3 | 12/2005 |
| WO | WO2005/112935 A1 | 12/2005 |
| WO | WO2005/113556 A1 | 12/2005 |
| WO | WO2005/117889 A1 | 12/2005 |
| WO | WO2005/120511 A1 | 12/2005 |
| WO | WO2005/044181 A3 | 3/2006 |
| WO | WO2006/030032 A1 | 3/2006 |
| WO | WO2006/038865 A1 | 4/2006 |
| WO | WO2006/050501 A2 | 5/2006 |
| WO | WO 2006/050946 | 5/2006 |
| WO | WO2006/068760 A2 | 6/2006 |
| WO | WO2004/087053 A3 | 8/2006 |
| WO | WO2006/089106 A2 | 8/2006 |
| WO | WO2006/108107 A1 | 10/2006 |
| WO | WO2006/112666 A1 | 10/2006 |
| WO | WO2005/074603 A3 | 11/2006 |
| WO | WO2006/114064 A2 | 11/2006 |
| WO | WO2006/114065 | 11/2006 |
| WO | WO 2006/114180 A1 | 11/2006 |
| WO | WO2006/068760 A3 | 12/2006 |
| WO | WO2006/089106 A3 | 12/2006 |
| WO | WO2007/002293 A2 | 1/2007 |
| WO | WO2007/006547 A1 | 1/2007 |
| WO | WO2007/020046 A1 | 2/2007 |
| WO | WO2007/002293 A3 | 3/2007 |
| WO | WO2007/025090 A2 | 3/2007 |
| WO | WO2006/050501 A3 | 5/2007 |
| WO | WO-2007/057466 A1 | 5/2007 |
| WO | WO2007/061737 A2 | 5/2007 |
| WO | WO2006/114064 A3 | 6/2007 |
| WO | WO2006/114065 A3 | 6/2007 |
| WO | WO2007/025090 A3 | 6/2007 |
| WO | WO2007/075554 A2 | 7/2007 |
| WO | WO2007/079164 A2 | 7/2007 |
| WO | WO 2007/095223 A2 | 8/2007 |
| WO | 2007/106503 A2 | 9/2007 |
| WO | WO2007/075554 A3 | 9/2007 |
| WO | WO2007/079164 A3 | 9/2007 |
| WO | WO2007/103308 A2 | 9/2007 |
| WO | WO2007/112005 A2 | 10/2007 |
| WO | WO2007/114926 A2 | 10/2007 |
| WO | WO2007/121453 A2 | 10/2007 |
| WO | WO2007/121920 A2 | 11/2007 |
| WO | WO2007/121924 A2 | 11/2007 |
| WO | WO2007/124854 A1 | 11/2007 |
| WO | WO2007/125310 A2 | 11/2007 |
| WO | WO2007/125315 A2 | 11/2007 |
| WO | WO2007/126841 A2 | 11/2007 |
| WO | WO2007/134828 A1 | 11/2007 |
| WO | WO2007/135380 A2 | 11/2007 |
| WO | WO2007/135398 A1 | 11/2007 |
| WO | WO2007/061737 A3 | 12/2007 |
| WO | WO2007/125315 A3 | 12/2007 |
| WO | WO2007/121920 A3 | 1/2008 |
| WO | WO2007/103308 A3 | 2/2008 |
| WO | WO2007/112005 A3 | 2/2008 |
| WO | WO2007/125310 A3 | 3/2008 |
| WO | WO2008/025755 A1 | 3/2008 |
| WO | WO 2008/037477 A1 | 4/2008 |
| WO | WO2008/047821 A1 | 4/2008 |
| WO | WO2008/063625 A2 | 5/2008 |
| WO | WO2008/064018 A1 | 5/2008 |
| WO | WO2007/121453 A3 | 7/2008 |
| WO | WO2007/135380 A3 | 7/2008 |
| WO | WO2008/063625 A3 | 7/2008 |
| WO | WO2008/079028 A1 | 7/2008 |
| WO | WO2008/082487 A2 | 7/2008 |
| WO | WO2008/094737 A2 | 8/2008 |
| WO | WO2007/121924 A3 | 9/2008 |
| WO | WO2008/112715 A2 | 9/2008 |
| WO | WO2007/114926 A3 | 10/2008 |
| WO | WO2008/118454 A2 | 10/2008 |
| WO | WO2008/118455 A1 | 10/2008 |
| WO | WO2008/118468 A1 | 10/2008 |
| WO | WO2008/125014 A1 | 10/2008 |
| WO | WO2008/125207 A1 | 10/2008 |
| WO | WO2008/127226 A2 | 10/2008 |
| WO | WO2007/126841 A3 | 11/2008 |
| WO | WO2008/112715 A3 | 11/2008 |
| WO | WO2008/118454 A3 | 11/2008 |
| WO | WO2008/136457 A1 | 11/2008 |
| WO | WO2008/082487 A3 | 12/2008 |
| WO | WO2008/127226 A3 | 12/2008 |
| WO | WO2009/000412 A1 | 12/2008 |
| WO | WO2009/004621 A1 | 1/2009 |
| WO | WO2009/010925 A2 | 1/2009 |
| WO | WO2009/023718 A2 | 2/2009 |
| WO | WO2008/094737 A3 | 3/2009 |
| WO | WO2009/023718 A3 | 4/2009 |
| WO | WO2009/044707 A1 | 4/2009 |
| WO | WO 2009/050506 | 4/2009 |

(56) References Cited

FOREIGN PATENT DOCUMENTS

| | | |
|---|---|---|
| WO | WO 2009/062118 A2 | 5/2009 |
| WO | WO2009/064802 A2 | 5/2009 |
| WO | WO2009/010925 A3 | 7/2009 |
| WO | WO2009/064802 A3 | 7/2009 |
| WO | WO2009/088986 A1 | 7/2009 |
| WO | WO2009/088990 A1 | 7/2009 |
| WO | WO2009/100406 A2 | 8/2009 |
| WO | WO2009/117157 A1 | 9/2009 |
| WO | WO2009/050506 A3 | 11/2009 |
| WO | WO2009/100406 A3 | 11/2009 |
| WO | WO-2010/006072 A2 | 1/2010 |
| WO | WO-2010/006072 A3 | 1/2010 |
| WO | WO2010/009207 A1 | 1/2010 |
| WO | WO2010/019210 A2 | 2/2010 |
| WO | WO2010/036380 A1 | 4/2010 |
| WO | WO2010/039534 A2 | 4/2010 |
| WO | WO 2010/045542 A2 | 4/2010 |
| WO | WO2010/019210 A3 | 5/2010 |
| WO | WO-2010/051042 A1 | 5/2010 |
| WO | WO-2010/051043 A1 | 5/2010 |
| WO | 2010/039534 A3 | 8/2010 |
| WO | WO-2012/151562 A1 | 11/2012 |
| WO | WO-2012/154695 A2 | 11/2012 |
| WO | WO-2012/154695 A3 | 11/2012 |

OTHER PUBLICATIONS

International Search Report dated Aug. 27, 2008 for International Application No. PCT/US07/08395, 4 pages.
Supplementary European Search Report dated Feb. 24, 2010 for EP Application No. 07754845, 4 pages.
International Search Report dated Sep. 25, 2008 for International Application No. PCT/US07/08355, 1 page.
International Search Report dated Oct. 2, 2006 for International Application No. PCT/US05/042524, 7 pages.
International Search Report Dated Apr. 5, 2006 for international Application No. PCT/FR2005/051073, 3 pages.
European Search Report Dated Feb. 4, 2011 for EP Application No. 05857011.0, 5 pages.
Kallberg, Y., et al. "Short-Chain Dehydrogenases/Reductases (SDRs)", *Eur. J. Biochem.* (2002) 269:4409-4417.
"Report of the Expert Committee on the Diagnosis and Classification of Diabetes Mellitus", *Diabetes Care* (1992) 2(Suppl 1):S5-S19.
Andrews, R.C., et al. "Effects of the 11β-Hydroxysteroid Dehydrogenase Inhibitor Carbenoxolone on Insulin Sensitivity in Men with Type 2 Diabetes", *J. Clin. Endocrinol. Metab.* (2003) 88(1):285-291.
Arnold, et al. "Pyrrolo[2,3-*d*]pyrimidines containing an extended 5-substituent as potent and selective inhibitors of Ick I", *Bioorg. & Med. Chem. Lett* (2000) 10:2167-70.
Banker, G.S., et al. *Modern Pharmaceutics*, 3ed, Marcel Dekker, New York, 1996, pp. 451-596.
Barf, T. et al. "Arylsulfonamidothiazoles as a New Class of Potential Antidiabetic Drugs. Discovery of Potent and Selective Inhibitors of the 11β-Hydroxysteroid Dehydrogenase Type 1", *J. Med. Chem.* (2002) 45(18):3813-3815.
Barnes, P.J., et al. "Efficacy and Safety of Inhaled Corticosteroids in Asthma", *Am. Rev. Respir. Dis.* (1993) 148:S1-26.
Bell, G., et al. "Glucokinase Mutations Insulin Secretion, and Diabetes Mellitus", *Annu. Rev. Physiol.*, (1996) 58:171-186.
Bishop, A.C. et al. "Generation of monospecific nanomolar tyrosine kinase inhibitors via a chemical genetic approach", Journal of the American Chemical Society, American Chemical Society, Washington, DC, US, vol. 121, No. 4, 1999, pp. 627-631.
Bohren, K.M., et al. "Expression, Crystallization and Preliminary Crystallographic Analysis of Human Carbonyl Reductase", *J. Mol. Biol.* (1994) 224:659-664.
Cox, B., et al. "Human Colorectal Cancer Cells Efficiently Conjugate the Cyclopentenone Prostaglandin, Prostaglandin $J_2$ to Glutathione", *Biochim. Biophys. Acta* (2002) 1584:37-45.

Diederich, S., et al. "In the Search for Specific Inhibitors of Human 11β-Hydroxysteroid-Dehydrogenases (11β-HSDs): Chenodeoxycholic Acid Selectively Inhibits 11β-HSD-I", *Eur. J. Endocrinol.* (2000) 142:200-207.
Ding, S., et al. "A Combinatorial Scaffold Approach Toward Kinase-Directed Heterocycle Libraries", *J. Am. Chem. Soc.* (2002) 124(8):1594-1596.
Ding, S., et al. "A Concise and Traceless Linker Strategy Toward Combinatorial Libraries of 2,6,9-Substituted Purines", *J. Org. Chem.* (2001) 66:8273-8276.
Ding, S., et al. "Resin-Capture and Release Strategy Toward Combinatorial Libraries of 2,6,9-Substituted Purines", *J. Comb. Chem.*(2002) 4:183-186.
Fajans, S., et al. "Maturity Onset Diabetes of the Young (MODY)", *Diabet. Med.* (1996) 13:S90-S95.
Feinstein, M.B., et al. "Regulation of the Action of Hydrocotisone in Airway Epithelial Cells by 11β-Hydroxysteroid Dehydrogenase", *Am. J. Respir. Cell. Mol. Biol.* (1999) 21:403-408.
Fingl, E., et al. "General Principles", *The Pharmacological Basis of Therapeutics, Fifth Edition* (1975), Ch. 1, 1-46.
Forrest, G.L., et al. "Induction of a Human Carbonyl Reductase Gene Located on Chromosome 21", *Biochim. Biophys. Acta.* (1990) 1048:149-155.
Forrest, G.L., et al. "Carbonyl Reductase", *Chem. Biol. Interact.* (2000) 129:21-40.
Franzen, R. "The Suzuki, the Heck, and the Stille reaction—three versative methods for the introduction of new C—C bonds on solid support", *Can J. Chem.* (2000) 78:957-962.
Funder, J.W., et al. "Mineralocorticoid Action: Target Tissue Specificity Is Enzyme, Not Receptor, Mediated", *Science* (1998) 242:583-585.
Garber, M.E., et al. "Diversity of Gene Expression in Adenocarcinoma of the Lung", *Proc. Nat. Acad. Sci. USA* (2001) 98(24):13784-13789.
Gonzalez, B., et al. "Protection against Daunorubicin Cytotoxicity by Expression of a Cloned Human Carbonyl Reductase cDNA in K562 Leukemia Cells", *Cancer Res.* (1995) 55:4646-4650.
Haase, A.,et al. "Detection of Viral Nucleic Acids by in Situ Hybridization", *Methods in Virology* (1984) VII:189-226.
Hanefeld, U., et al. "One-pot Synthesis of Tetrasubstituted Pyrazoles Proof of Regiochemistry", *J. Chem. Soc. Perkin Trans.* (1996) 1:1545-1552.
Ishiyama, T., et al. "A Stoichiometric Aromatic C—H Borylation Catalyzed by Iridium(I)/2,2'-Bipyridine Complexes at Room Temperature", *Angew. Chem. Int. Ed.* (2002) 41(16):3056-3058.
Ishiyama, T., et al. "Mild Iridium-Catalyzed Borylation of Arenes. High Turnover Numbers, Room Temperature Reactions, and Isolation of a Potential Intermediate", *J. Am. Chem. Soc.* (2002) 124(3):390-391.
Kallberg, Y., et al. "Short-Chain Dehydrogenase/Reductase (SDR) Relationships: a Large Family with Eight Clusters Common to Human, Animal, and Plant Genomes", *Protein Sci.* (2002) 11:636-641.
Knight, et al. "A Pharmacological Map of the P13-K Family Defines a Role for p110α in Insulin Signaling", *Cell* (2006) 125:733-747.
Kwok, B.H., et al. "The Anti-Inflammatory Natural Product Parthenolide from the Medicinal Herb Feverfew Directly Binds to and Inhibits IkB Kinase", *Chem. Biol.* (2001) 8:759-766.
Kraybill, B.C. et al. "Inhibitor scaffolds as new allele specific kinase substrates", Journal of the American Chemical Society, American Chemical Society, Washington, DC, US, vol. 124, No. 41, Oct. 16, 2002, pp. 12118-12128.
Mayer, T.U., et al. "Small Molecule Inhibitor of Mitotic Spindle Bipolarity Identified in a Pheontype-Based Screen", *Science* (1999) 286:971-974.
Moon, H.S., et al. "A Novel Microtubule Destabilizing Entity from Orthogonal Synthesis of Triazine Library and Zebrafish Embryo Screening", *J. Am. Chem. Soc.* (2002) 124:11608-11609.
Nakanishi, M., et al. "Cloning and Sequence Analysis of a cDNA Encoding Tetrameric Carbonyl Reductase of Pig Lung", *Biochem. Biophys. Acta* (1993) 194(3):1311-1316.

(56) References Cited

OTHER PUBLICATIONS

Niswender, C.M., et al. "Protein Engineering of Protein Kinase A Catalytic Subunits Results in the Acquisition of Novel Inhibitor Sensitivity", *The Journal of Biological Chemistry* (2002) 277(32):28916-28922.

Nobel, C.S.I., et al. "Purification of Full-Length Recombinant Human and Rat Type 1 11β-hydroxysteroid Dehydrogenases with Retained Oxidoreductase Activities", *Protein Expr. Purif.* (2002) 26:349-356.

Miyaura, N., et al., "Palladium-Catalyzed Cross-Coupling Reactions of Organoboron Compounds," *Chem. Rev.* (1995) 95(7):2457-2483.

Oppermann, U.C., et al. "Forms and Functions of Human SDR Enzymes", *Chem. Biol. Interact.* (2001) 130-132(1-3):699-705.

Persson, C.G. "Glucocorticoids for Asthma—Early Contributions", *Pulm. Pharmacol.* (1989) 2:163-166.

Pudlo, J.S., et al. "Synthesis, Antiproliferative, and Antiviral Activity of Certain 4-Substituted and 4,5 Disubstituted 7[1,3-Dihydroxy-2-propoxy)methyl]pyrrolo[2,3-d]pyrimidines", *J. Med. Chem.* (1990) 33:1984-1992.

Robertson, R.P. "Eicosandoids and Human Disease", *Harrison's Principles of Internal Medicine*, Isselbacher K.J., et al. (eds.), McGraw-Hill, New York City (1994) 1:431-435.

Romero, D.G., et al. "Cloning and Expression of the Bovine 11β—hydroxysteroid Dehydrogenase Type-2", *J. Steroid Biochm. Mol. Biol.* (2000) 72:231-237.

Singer, R.H., et al. "Optimization of in situ Hybridization Using Isotopic and Non-Isotopic Detection Methods", *Biotechniques* (1986) 4(3):230-250.

Soldan, M., et al. "Induction of Daunorubicin Carbonyl Reducing Enzymes by Daunorubicin in Sensitive and Resistant Pancreas Carcinoma Cells", *Biochem. Pharmacol.* (1996) 51:117-123.

Tanaka, M., et al. "An Unbiased Cell Morphology-Based Screen for New, Biologically Active Small Molecules", *PLoS Biology* (2005) 3(5):0764-0776.

Ugarkar, B.G., et al. "Adenosine Kinase Inhibitors. 2. Synthesis, Enzyme Inhibition, and Antiseizure Activity of Diaryltubercidin Analogues", *J. Med. Chem.* (2000) 43:2894-2905.

White, P.C., et al. "11β—Hydroxysteroid Dehydrogenase and the Syndrome of Apparent Mineralocorticoid Excess", *Endocr. Rev.* (1997) 18(1):135-156.

Widler, L., et al. "7-Alkyl- and 7-Cycloalkyl-5-aryl-pyrrolo[2,3-d]pyrimidines—Potent Inhibitors of the Tyrosine Kinase c-Src," *Bioorganic & Medicinal Chemistry Letters* (2001) 11(6):849-852.

Wolff, M. E. *Burger's Medicinal Chemistry*, 5ed, Part 1, John Wiley & Sons, 1995, pp. 975-977.

U.S. Appl. No. 13/016,957, filed Jan. 28, 2011, Tanaka et al.

U.S. Appl. No. 13/112,611, filed May 20, 2011, Ren et al.

U.S. Appl. No. 13/289,540, filed Nov. 4, 2011, Ren et al.

Ames et al., "Heterocyclic Synthesis from o-Halogen-acids. Part II. Thienopyridinones and Thienopyranones from 3- bromothiophene -2- and 4-Bromothiophene-3-Carboxylic Acids", Journal of the Chemical Society, Perkin Transactions 1, Jan., 14:1390-1395 (1975).

Basotest®, "Test Kit for the Quantitative Determination of the Degranulation of Basophilic Granulocytes in Heparinized Human Whole Blood", [www.biocarta.com/TDS/10-0500.pdf], Retreived from the Internet Nov. 29, 2011, 10 pages.

Cámpora, et al. Binuclear complexes of nickel bridged by hydrocarbon ligands. Isocyanide insertion chemistry and amide formation by intramolecular coupling of acyl and imidoyl functionalities. Organometallics. Jan. 1992;11(1):11-13.

Cámpora, et al. Isocyanide insertion chemistry. Synthesis and structural characterization of bridging imidoyl complexes of nickel and amide formation by intramolecular coupling of acyl and imidoyl functionalities. Organometallics. Oct. 1993;12(10):4025-31.

Chaisuparat, et al. Dual Inhibition of PI3K(alpha) and mTOR as an Alternative Treatment for Kaposi's Sarcoma. Cancer Research. 2008;68:8361.

Chappelow, et al. Neovascular Age-Related Macular Degeneration: Potential Therapies. Drugs. 2008;68(8):1029-1036.

Davis, et al. The Preparation of Substituted 1(2H)-Isoquinolinones from Dilithiated 2-Methyl-N-arylbenzamides, 2-Methyl-N-(arylmethyl)-benzamides, or 2-Methylbenzoic Acid, 2,2-Dimethylhydrazide. Synthetic Communications. Sep. 1997;27(17):2961-9.

Dijksman, et al. 271. 1 : 2-Dihydro-2-thianaphthalene derivatives. Part I. Preparation and reactions of 1 : 2-dihydro-1-keto-2-thianaphthalenes. J. Chem. Soc. 1951:1213-18.

Donati. Emerging Therapies for Neovascular Age-Related Macular Degeneration: State of the Art. Ophthalmologica. 2007;221:366-377.

European search report and search opinion dated Oct. 26, 2011 for Application No. 9700424.6, 5 pages.

European Search Report dated Mar. 1, 2010 for EP Application No. 07873406.8, 5 pages.

Extended European Search Report from corresponding European Application No. 09700784.3 dated Oct. 28, 2011, 6 pages.

Graupera, et al. Angiogenesis selectively requires the p110 isoform of PI3K to control endothelial cell migration. Nature. 2008;453:662-666.

Hellwinkel, et al. Heterocyclensynthesen mit MF/Al2O3-Basensystemen: 2-Arylbenzofurane and 2,3-Diarylisochinolin-1(2H)-one. Synthesis. 1995;1995(9):1135-41.

International Preliminary Report on Patentability from International Application No. PCT/US2009/000042 issued Jul. 6, 2010, 9 pages.

International search report and written opinion dated Aug. 22, 2011 for PCT/US2011/037412, 2 pages.

International search report and written opinion dated Nov. 20, 2009 for PCT/US2009/005380, 9 pages.

International search report dated Nov. 2, 2010 for PCT Application No. PCT/US10/02020, 8 pages.

International search report dated Mar. 11, 2009 for PCT Application No. PCT/US2009/00038, 1 page.

International search report dated Mar. 23, 2009 for PCT Application No. PCT/US2009/00042, 2 pages.

Kajita, et al. Nickel-catalyzed decarbonylative addition of phthalimides to alkynes. J Am Chem Soc. May 14, 2008;130(19):6058-9.

Kost et al., "Recyclization of 3-Alkyl- and 1,3-Dialkylisoquinolinium Salts to Naphthylamines", Chemistry of Heterocyclic Compounds, Jan., 16(9):965-970 (1981).

Kumar et al., "Keten Dithioacetals. Part II. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine Derivatives", Journal of the Chemical Society, Perkin Transactions 1, Chemical Society, Letchworth, Jan., 8:857-862 (1978).

Kundu, et al. Palladium-Catalysed Heteroannulation with Terminal Alkynes: a Highly Regio- and Stereoselective Synthesis of (Z)-3-Aryl(alkyl)idene Isoindolin-1-ones1. Tetrahedron. Jun. 30, 2000;56(27):4777-92.

Lee, et al. All roads lead to mTOR: integrating inflammation and tumor angiogenesis . . . Cell Cycle. 2007;6(24):3011-3014.

Majumder, et al. mTOR inhibition reverses Akt-dependent prostate intraepithelial neoplasia through regulation of apoptotic and HIF-1-dependent pathways. Nature Medicine. 2004;10:594-601.

Mellinghoff, et al. TORward AKTually useful mouse models. Nature Medicine. 2004;10:579-580.

Modi, et at. Isoquinolones: Part IV—Synthesis of 3-Methyl, 3-Formyl & Other 3-Substituted N-Arylisoquinolones, Indian J. Chem. 1979; 18B:304-306.

Nemazanyi, et al. 3-Amino-4-aryl-1(2H)-isoquinolones. Chemistry of Heterocyclic Compounds. Mar. 1991;27(3):307-8.

Oda, et al. PIK3CA Cooperates with Other Phosphatidylinositol 3'-Kinase Pathway Mutations to Effect Oncogenic Transformation. Cancer Research. 2008;68:8127.

Ozaki, et al. Studies on 4 (1H)-Quinazolinones. IV. Convenient Syntheses of 12-Methyl-6H-isoquino [2,1-a] quinazolin-6-one and 6-Methyl-13H-quinazolino [3,4-a] quinazolin-13-one. Chem. Pharm. Bull. Jun. 25, 1984;32(6):2160-4.

(56) References Cited

OTHER PUBLICATIONS

Ozol, et al. Autoxidative transformations of 2-substituted 3-alkyl-4-hydroxy-1-oxo-1, 2-dihydroisoquinolines. Chemistry of Heterocyclic Compounds. Jun. 1978;14(6):644-8.
Patel, et al. Immunopathological aspects of age-related macular degeneration. Seminars in Immunopathology. 2008;30(2):97-110.
Stanoeva et al. Homophthalic anhydrides and their application to the synthesis of heterocyclic compounds (review). Chemistry of Heterocyclic Compounds. Dec. 1984;20(12);1305-15.
Supplementary European Examination Report dated Sep. 20, 2011 for EP Application No. 07754845.1, 4 pages.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6):1229-1233 (2002).
Vasilevsky et al., "Unexpected results in the heterocyclization of 5-acetylenylpyrazole4-carboxylic acid hydrazides under the influence of CuCl: formatin of a diazepinone and dehydrodimerization into the corresponding bis(pyrazolo [4,3-d] [1,2] diazepinone)", Tetrahedron Letters, Jan., 46(26): 4457-4459 (2005).
Yaguchi, et al. Antitumor activity of ZSTK474, a new phosphatidylinositol 3-kinase inhibitor. J. Natl. Cancer. Inst. 2006; 98(8): 545-556. Abstract only.
Abdel-Mohsen, S.A., "Synthesis, reactions and antimicrobial activity of 2-amino-4-(8-quinolinol-5-yl)-1-(p-tolyl)-pyrrole-3-carbonitrile", Bull. Korean Chem. Soc. 2005 26(5):719-728.
Beeram, M. et al., "Akt-induced endocrine therapy resistance is reversed by inhibition of mTOR signaling", Annals of Oncology 18:1323-1328, 2007.
European Examination Report dated Sep. 14, 2011 for EP Application No. 07873406.8, 4 pages.
Feldman, M.E. et al. , "Active site inhibitors of mTOR target rapamycin-resistant outputs of mTORC1 and mTORC2", PLOS Biology 7(2):371-383, Feb. 2009.
International Preliminary Report on Patentability and Written Opinion dated Apr. 19, 2011 for International Application No. PCT/US2009/060985, 6 pages.
International Preliminary Report on Patentability and Written Opinion dated Jan. 1, 2011 for International Application No. PCT/US2009/049969, 7 pages.
International Preliminary Report on Patentability and Written Opinion dated May 22, 2007 for International Application No. PCT/US2005/042524, 12 pages.
International Preliminary Report on Patentability and Written Opinion dated Nov. 4, 2008 for International Application No. PCT/US2007/008355, 7 pages.
International Preliminary Report on Patentability and Written Opinion dated Oct. 8, 2008 for International Application No. PCT/US2007/008395, 6 pages.
International Search Report dated Jun. 28, 2010 for International Application No. PCT/US2009/060985, 5 pages.
International Search Report dated Mar. 15, 2010 for International Application No. PCT/US2009/049969, 4 pages.
Kim, M. et al. , "Activation and function of the mTORC1 pathway in mast cells", The Journal of Immunology 180:4586-4595, Apr. 2008.
Supplementary European Search Report dated Feb. 16, 2010 for EP Application No. 07754845.1, 4 pages.
Supplementary European Search Report dated Sep. 20, 2011 for EP Application No. 07754845.1, 4 pages.
Takeuchi, H. et al. , "Synergistic augmentation of reapamycin-induced autophagy in malignant glioma cells by phosphatidylinositol 3-kinase/protein kinase B inhibitors", Cancer Research 65(8):3336-3346, Apr. 15, 2005.
Apsel, Beth et al., "Targeted polypharmacology: discovery of dual inhibitors of tyrosine and phosphoinositide kinases", Nature Chemical Biology 4(11):691-699, 2008.
Aragón, Anthony D. et al., "Characterization of Differentiated Quiescent and Nonquiescent Cells in Yeast Stationary-Phase Cultures", Molecular Biology of the Cell 19:1271-1280, 2008.
Aragón, Anthony D. et al., "Microarray based analysis of temperature and oxidative stress induced messenger RNA in Schistosoma mansoni", Molecular & Biochemical Parasitology 162:134-141, 2008.
Aragón, Tomas et al., "Messenger RNA targeting to endoplasmic reticulum stress signaling sites", Nature 457(7230):736-740, 2009.
Berge, Stephen M. et al., "Pharmaceutical Salts", Journal of Pharmaceutical Sciences Berge et al., "Pharmaceutical Salts", Journal of Pharmaceutical Sciences 66(1):1-19, 1977.
Bishop, Anthony C. et al., "Design of allele-specific inhibitors to probe protein kinase signalling", Current Biology 8:257-266, 1998.
Blethrow, Justin et al., "Design and Use of Analog-Sensitive Protein Kinases", Current Protocols in Molecular Biology 18.11.1-18.11.19, 2004.
Cannon, J.G., "Analog Design", Burger's Medicinal Chemistry and Drug Discovery, Fifth Edition, vol. 1: Principles and Practice, 1995, pp. 783-802.
Carrasco, Daniel R. et al., "The Differentiation and Stress Response Factor XBP-1 Drives Multiple Myeloma Pathogenesis", Cancer Cell 11:349-360, 2007.
Cox, Jeffery S. et al., "A Novel Mechanism for Regulating Activity of a Transcription Factor That Controls the Unfolded Protein Response", Cell 87:391-404, 1996.
Credle, Joel J. et al., "On the mechanism of sensing unfolded protein in the endoplasmic reticulum", Proceedings of the National Academy of Sciences 102(52):18773-18784, 2005.
Dar, Arvin C. et al., "Small Molecule Recognition of c-Src via the Imatinib-Binding Conformation", Chemistry & Biology 15:1015-1022, 2008.
Doody, Gina M. et al., "BLIMP-1 is a target of cellular stress and downstream of the unfolded protein response", European Journal of Immunology 36:1572-1582, 2006.
Extended European Search Report from corresponding European Application No. 12175020.2 dated Jan. 1, 2013, 7 pages.
Extended European Search Report from corresponding European Application No. 12175019.4 dated Apr. 4, 2013, 12 pages.
Gonzalez, Tania N. et al., "Ire1p: A Kinase and Site-Specific Endoribonuclease", Methods in Molecular Biology 160:25-36, 2001.
International Preliminary Report on Patentability and Written Opinion dated Apr. 17, 2012 for International Application No. PCT/US2010/053072, 5 pages.
International Preliminary Report on Patentability and Written Opinion dated Mar. 4, 2014 for International Application No. PCT/US2012/053542, 10 pages.
International Search report dated Jul. 4, 2011 for International Application No. PCT/US2010/053072, 5 pages.
International Search Report and Written Opinion dated Jun. 28, 2013 for International Application No. PCT/US2012/053542, 13 pages.
Kimata, Yukio et al., "Two regulatory steps of ER-stress sensor Ire 1 involving its cluster formation and interaction with unfolded proteins", The Journal of Cell Biology 179(1):75-86, 2007.
Koong, Albert C. et al., "Targeting XBP-1 as a Novel Anti-Cancer Strategy", Cancer Biology & Therapy 5(7):756-759, 2006.
Kudo, Takashi et al., "The Unfolded Protein Response Is Involved in the Pathology of Alzheimer's Disease", New York Academy of Sciences 977:349-355, 2002.
Lee, Kenneth P.K. et al., "Structure of the Dual Enzyme Ire1 Reveals the Basis for the Catalysis and Regulation in Nonconventional RNA Splicing", Cell 132:89-100, 2008.
May, Yanjun et al., "The role of the unfolded protein response in tumour development: friend or foe?", Nature Reviews Cancer 4:966-977, 2004.
Naidoo, Nirinjini et al., "Sleep deprivation induces the unfolded protein response in mouse cerebral cortex", Journal of Neurochemistry 92:1150-1157, 2005.
Papa, Feroz R. et al., "Bypassing a Kinase Activity with an ATP-Competitive Drug", Science 302:1533-1537, 2003.
Shamu, Caroline E. et al., "Oligomerization and phosphorylation of the Ire1p kinase during intracellular signaling from the endoplasmic reticulum to the nucleus", The EMBO Journal 15(12):3028-3039, 1996.

(56) References Cited

OTHER PUBLICATIONS

Sheridan, R.P., "The Most Common Chemical Replacements in Drug-Like Compounds". *J. Chem. Inf. Comput. Sci.* 2002, 42:103-108.

Tseng, Ping-Hui et al., "Synergistic interactions between imatinib mesylate and the novel phosphoinositide-dependent kinase-1 inhibitor OSU-03012 in overcoming imatinib mesylate resistance", *Blood* 105:4021-4027, 2005.

Walker et al., "Structural Determinants of Phosphoinositide 3-Kinase Inhibition by Wortmannin, LY294002, Quercetin, Myricetin, and Staurosporine", *Molecular Cell* 2000, 6(4):909-919.

West et al., "Activation of the PI3K/Akt pathway and chemotherapeutic resistance," *Drug Resistance Updates*, 5, 2002, 234-248.

Wymann, et al., "Wortmannin Inactivates Phosphoinositide 3-Kinase by Covalent Modification of Lys-802, a Residue Involved in the Phosphate Transfer Reaction", Molecular and Cellular Biology 1996, 16(4):1722-1733.

Yaguchi, et al., "A novel phosphatidylinositol 3-kinase inhibitor, ZSTK474 exterted antitumor activity against human tumor xenografts by oral administration", Proc. Amer. Assoc. Cancer Res. 2005, 46:1691 (Abstract).

Yoshida, Hiderou et al., "XBP1 mRNA Is Induced by ATF6 and Spliced by IRE1 in Response to ER Stress to Produce a Highly Active Transcription Factor", *Cell* 107:881-891, 2001.

Zhang, Xuewu et al., "An Allosteric Mechanism for Activation of the Kinase Domain of Epidermal Growth Factor Receptor", *Cell* 125:1137-1149, 2006.

Zheng, Yi et al., "Hepatitis C Virus Non-structural Protein NS4B Can Modulate an Unfolded Protein Response", *The Journal of Microbiology* 43(6):529-536, 2005.

Abdul-Majeed, S. et al. (2011). "Polycystic Disease in Visceral Organs," *Obstetrics and Gynecology International* 7 pages.

Braun, M. et al. (Mar. 15, 2012). "Ovarian toxicity from sirolimus," *New England Journal of Medicine* 366(11):1062-1064.

McKee, B. et al. (2005). "Rapamycin-Induced Amelioration of Murine Polycystic Kidney Disease," *Experimental Biology IUPS 2005: Meeting Abstracts* A244, Abstract 197.18, 2 pages.

Shiilingford, J.M. et al. (Apr. 4, 2006, e-published Mar. 27, 2006). "The mTOR pathway is regulated by polycystin-1, and its inhibition reverses renal cystogenesis in polycystic kidney disease," 103(14):5466-5471.

Wahl, P.R. et al. (Mar. 2006, e-published Oct. 12, 2005). "Inhibition of mTOR with sirolimus slows disease progression in Han:SPRD rats with autosomal dominant polycystic kidney disease (ADPKD)," *Nephrol Dial Transplant* 21(3):598-604.

Wüthrich, R.P. et al. (Jun. 2014, e-published Mar. 28, 2014). "Pharmacological management of polycystic kidney disease," *Expert Opin Pharmacother* 15(8):1085-1095.

Wu, T.Y. H. et al. (Oct. 2, 2003). "One-pot two-step microwave-assisted reaction in constructing 4,5-disubstituted pyrazolopyrimidines," *Org Lett.* 5(20):3587-3590.

\* cited by examiner

A
Targets and Pathways Detected in BioMAP® Systems

Kinases
- p38 MAPK
- MEK
- JNK
- mTOR
- PI-3K
- JAK
- Lck
- GSK-3αβ
- c-Raf
- CaMK-II
- PKG
- PKA
- Cdks
- Casein Kinase II
- IKK2
- Rho Kinase

GPCRs
- PAF receptor
- HI Histamine receptors
- β-andrenergic receptor (antagonists & agonists)
- PAR receptors

Nuclear Hormone Receptors
- Glucocorticoid receptor
- Estrogen receptor
- Androgen receptor
- PPAR
- RAR/RXR
- FXR

Enzymes
- Cydooxygenases
- Calcineurin
- DCODH
- IMPDH
- Phosphodiesterases
- HMG-CoA reductase
- Guanylyl cyclase
- Proteasome
- Histone deacetylase
- Aminopeptidase
- Angiotensin converting enzyme
- Farnesyl transferase
- HO-1

Biologies
- TNF-α antagonists
- IL-1αβ antagonists
- IL-10
- IL-4
- IFN-γ antagonists
- TGF-β

Other
- Hsp-90 inhibitors
- L-type Ca++ channel
- Na+/Ca++ exchange
- Ca++ flux
- Antioxidants
- NF-kB antagonists

B

| System | Environment | Cell Types | Readouts | |
|---|---|---|---|---|
| 3C | IL-1β+ TNFα+ IFN-γ | HUVEC | E-selectin, ICAM, VCAM, MIG | IL-8, HLA-OR, MCP-1 |
| 4H | IL-4 + Histamine | HUVEC | P-selectin, VEG-2, VCAM, uPAR | CD55, Eotaxin-3, MCP-1 |
| LPS | LPS (TL/W) | HUVEC + IPBMC | VCAM, CD14, TF, CD40, CD69 | MCP-1, E-selectin, IL-1α, IL-8, M-CSF |
| SAG | SEB + TSST (TCR) | HUVEC + PBMC | CD38, CD40, CD69, MIG | E-selectin, IL-8, MCP-1 |

FIG. 1

SUBSTITUTED PYRAZOLO[3,4-D] PYRIMIDINES AS ANTI-INFLAMMATORY AGENTS

CROSS-REFERENCES TO RELATED APPLICATIONS

This application claims the benefit of U.S. Provisional Patent Application No. 60/629,639, filed Nov. 19, 2004, which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under grant AI 044009 awarded by the National Institutes of Health. The Government has certain rights in the invention.

BACKGROUND OF THE INVENTION

Protein kinases are involved in a wide variety of cellular processes, such as growth factor response, cytokine response, immune response, stress response, and cell cycle regulation, to specify only a few such processes. Because their improper regulation is believed to cause various diseases including cancer and inflammation, protein kinases are important drug targets for the treatment of these diseases.

Inflammatory conditions, particularly chronic inflammatory diseases, are of particular interest to developers of new pharmaceutical products, because such conditions and diseases are widespread, and improved therapies for them are needed. These diseases are caused by action of the immune system, including the inappropriate activation of T cells, expression of regulatory cytokines and chemokines, loss of immune tolerance, and the like. Modulation of the immune response varies with the specific factors produced and the receptors present on the responding cell. Among these diseases are autoimmune and/or chronic inflammatory diseases, which include multiple sclerosis and inflammatory bowel diseases ("IBD," including ulcerative colitis and Crohn's disease), colitis, diseases of the joints, such as rheumatoid arthritis, diseases involving the destruction or improper alteration of nucleic acids, as observed with systemic lupus erythematosus and other diseases such as psoriasis, insulin dependent diabetes mellitus (IDDM), Sjogren's disease, myasthenia gravis, thyroid disease, Alzheimer's disease, uveitis, and cardiovascular disease.

Thus, there is a need in the art for effective anti-inflammatory compounds useful in the treatment of disease. The present invention addresses these and other needs.

BRIEF SUMMARY OF THE INVENTION

The present invention provides anti-inflammatory compounds useful in the treatment of diseases and conditions in which inflammation is involved in disease progression or the manifestation of symptoms of the disease or condition.

In one aspect, the present invention provides a compound represented by the following structural formula:

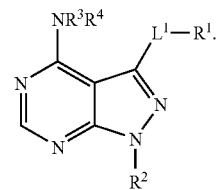

(I)

In Formula (I) above, $R^1$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$, $R^3$, and $R^4$ are, independently, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ and $R^4$ are optionally joined with the nitrogen to which they are attached to form a substituted or unsubstituted heterocycloalkyl or substituted or unsubstituted heteroaryl.

$L^1$ is a bond, substituted or unsubstituted alkylene, substituted or unsubstituted cycloalkylene, or substituted or unsubstituted heteroalkylene.

In another aspect, the present invention provides a method for treating or preventing a disorder characterized by abnormal inflammation, said method including administering to a subject a therapeutically effective amount of a compound of the present invention.

In another aspect, the present invention provides pharmaceutical formulations of a compound of the present invention, and methods for using such compounds and their pharmaceutical formulations in the treatment of inflammatory diseases and conditions.

In another aspect, the present invention provides methods for making the compounds and pharmaceutical formulations of the invention.

In another aspect, the present invention provides compounds and pharmaceutical formulations for use in the treatment of an inflammatory disease or condition.

In certain embodiments, the compounds of the invention are T cell activation inhibitors. In another embodiment, the compounds of the invention are monocyte activation inhibitors. In another embodiment, the compounds of the invention are gamma interferon signaling inhibitors.

BRIEF DESCRIPTION OF THE DRAWINGS

FIG. 1 illustrates four exemplary BioMAP™ (BioSeek, Inc., Burlingame, Calif.) inflammation model systems useful in detecting and discriminating modifiers of multiple targets and pathways, where panel (A) sets forth multiple therapeutically relevant targets and pathways that are detected and discriminated in BioMAP models, including a large number of kinases, and panel (B) provides details on the four exemplary model systems.

DETAILED DESCRIPTION OF THE INVENTION

Definitions

Figure 2:
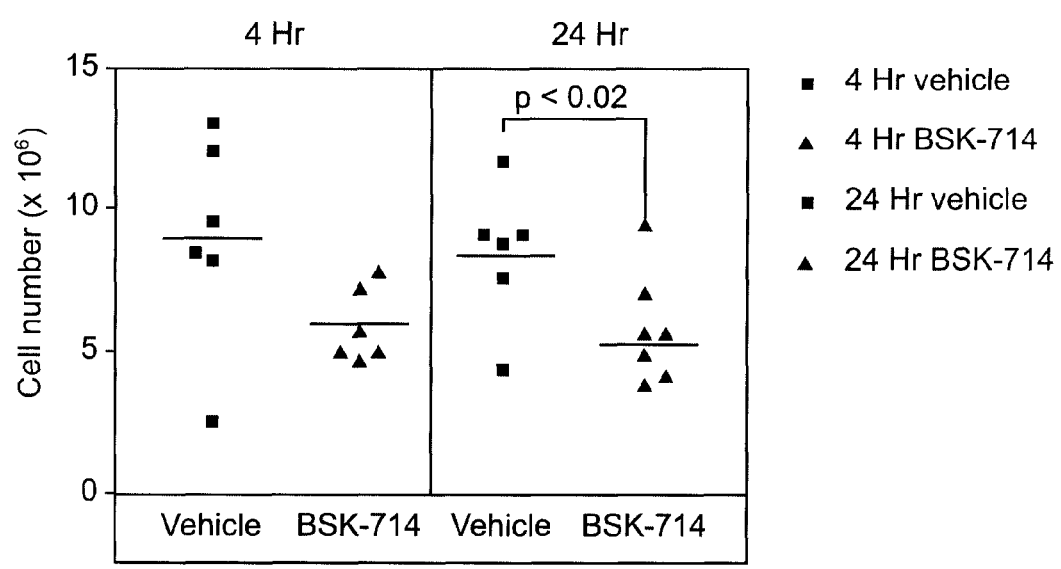
FIG. 2 illustrates the decrease in the number of recruited leukocytes in a mouse model of peritoneal inflammation resulting from the administration of an anti-inflammatory pyrazolopyrimidine of the present invention.

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e. unbranched) or branched chain, or cyclic hydrocarbon radical, or combination thereof, which may be fully saturated, or mono- or polyunsaturated, and can include di- and multivalent radicals, having the number of carbon atoms designated (i.e. C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, and the like. An unsaturated alkyl group is one having one or more double bonds or triple bonds or both. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, and 3-butynyl, as well as the higher homologs and isomers. Alkyl groups that are limited to hydrocarbon groups are termed "homoalkyl".

The term "alkylene," by itself or as part of another substituent, means a divalent radical derived from an alkyl, as exemplified, but not limited, by —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a straight or branched chain, or cyclic hydrocarbon radical, or combinations thereof, consisting of at least one carbon atom and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P, S and Si may be placed at any interior position of the heteroalkyl group or at the position at which alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Up to two heteroatoms may be consecutive, such as, for example, —CH$_2$—NH—OCH$_3$ and —CH$_2$—O—Si(CH$_3$)$_3$. Similarly, the term "heteroalkylene," by itself or as part of another substituent, means a divalent radical derived from heteroalkyl, as exemplified, but not limited to, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g. alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted as used herein as excluding specific heteroalkyl groups, such as —NR'R" or the like.

The term "alkoxy" refers to an alkyl attached to the remainder of the molecule via an oxygen heteroatom. The alkyl portion of the alkoxy group may be any appropriate length. In some embodiments, the alkyl portion of the alkoxy group is a C$_1$-C$_{20}$ alkyl (i.e. C$_1$-C$_{20}$ alkoxy). In some embodiments, the alkyl portion of the alkoxy group is a C$_1$-C$_{10}$ alkyl (i.e. C$_1$-C$_{10}$ alkoxy). In some embodiments, the alkyl portion of the alkoxy group is a C$_1$-C$_5$ alkyl (i.e. C$_1$-C$_5$ alkoxy).

An "alkylesteryl," as used herein, refers to a moiety having the formula R'—C(O)O—R", wherein R' is an alkylene moiety and R" is an alkyl moiety.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4 morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent derivatives of aryl and heteroaryl, respectively.

For brevity, the term "aryl" when used in combination with other terms (e.g., aryloxy, arylthioxy, arylalkyl) includes both aryl and heteroaryl rings as defined above in combination with another moiety. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Preferred substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in art will understand that the term "alkyl" is meant to include groups in which carbon atoms are bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$), and the like.

Similar to the substituents described for alkyl radicals above, exemplary substituents for aryl and heteroaryl groups (as well as their divalent derivatives) are varied and are selected from, for example and without limitation: —OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number, when present, ranging from one to the total number of open valences on aromatic ring system; and where R', R", R"' and R"" are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R"' and R"" groups when more than one of these groups is present.

Two of the substituents on adjacent atoms of an aryl or heteroaryl ring may optionally form a ring of the formula -T-C(O)-(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of an aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

A "substituent group," as used herein, means a group selected from the following moieties:
 (A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and
 (B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
   (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
   (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and each substituted or unsubstituted heterocycloalkyl is a substituted or unsubstituted 5 to 7 membered heterocycloalkyl.

The compounds of the present invention may exist as salts. Accordingly, the present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are in any event encompassed within the scope of the present invention. Certain compounds of the present invention may exist in multiple crystalline or amorphous forms. In general, all physical forms are equivalent or otherwise suitable for the uses contemplated by the present invention and are within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention includes compounds in their racemic and optically pure forms. Optically active (R)- and (S)-, or (D)- and (L)-isomers may be prepared using chiral synthons or chiral reagents, or resolved from mixtures using conventional techniques. When the compounds described herein contain olefinic bonds or other centers of geometric asymmetry, and unless specified otherwise, it is intended that the compounds include both E and Z geometric isomers.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired pharmaceutically acceptable base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired pharmaceutically acceptable acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of pharmaceutical Science,* 1977, 66, 1-19). Certain specific compounds of the present invention contain both basic and acidic functionalities that allow the compounds to be converted into either base or acid addition salts.

In addition to salt forms, the present invention provides compounds, which are in a prodrug form. Prodrugs of the compounds described herein are those compounds that readily undergo chemical changes under physiological conditions to provide the compounds of the present invention or one or more of their active metabolites. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

I. Anti-Inflammatory Compounds

In one aspect, the present invention provides a compound represented by the following structural formula:

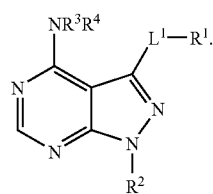

(I)

In Formula (I) above, $R^1$ is selected from substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$, $R^3$, and $R^4$ are, independently, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ and $R^4$ are optionally joined with the nitrogen to which they are attached to form a substituted or unsubstituted heterocycloalkyl or substituted or unsubstituted heteroaryl.

$L^1$ is a bond, substituted or unsubstituted alkylene, substituted or unsubstituted cycloalkylene, or substituted or unsubstituted heteroalkylene. In some embodiments, where $L^1$ is a bond, $R^2$ is t-butyl, and $R^3$ and $R^4$ are hydrogen, then $R^1$ is not para-methylphenyl. In some embodiments, where $L^1$ is a bond, $R^2$ is unsubstituted alkyl, and $R^2$ and $R^3$ are hydrogen, then $R^1$ is not methylphenyl.

In some embodiments, the compounds of Formula I do not include those compounds set forth in U.S. Pat. No. 5,593,997, U.S. Pat. No. 6,383,790, U.S. Pat. No. 5,981,533, U.S. Pat. No. 6,521,417, U.S. Pat. No. 6,921,763, U.S. Pat. No. 6,713,474, U.S. Pat. No. 6,660,744, USP Application 2002/0156081, USP Application 2003/0073218, USP Application 2005/0085472, each of which are incorporated by reference in their entirety for all purposes. In some embodiments, the compounds of the invention are compounds other than the specific compounds set forth in the aforementioned patents and published patent applications.

In some embodiments, the compounds of the invention are the subset of compounds of the compounds of Formula (I) that do not displace staurosporine from a protein kinase where the compound is present at a concentration of less than or equal to 10 μM. In some embodiments, the compounds of the invention are the subset of compounds of the compounds of Formula (I) that do not inhibit or significantly decrease protein kinase activity when contacted with the kinase at a concentration of less than or equal to 10 μM. In some related embodiments, the compounds of the invention are the subset of compounds of the compounds of Formula (I) that do not decrease protein kinase activity more than 1%, 5%, 10%, 15%, 20%, 25%, 30%, 35%, 40%, 45%, or 50%, relative to the kinase activity in the absence of the compound. In some related embodiments, the compound that does not displace staurosporine as described above and/or does not inhibit or substantially decrease the activity of a protein kinase as described above, is a compound of Formula (I) wherein $R^1$ is a substituted phenyl (e.g. substituted with a halogen), $R^3$ and $R^4$ are hydrogen or unsubstituted $C_1$-$C_{10}$ alkyl, $L^1$ is a bond or unsubstituted $C_1$-$C_{10}$ alkylene, and $R^2$ is unsubstituted $C_1$-$C_{10}$ alkyl. In a further related embodiment, $R^1$ is a halophenyl, $R^3$ and $R^4$ are hydrogen or methyl, $L^1$ is unsubstituted $C_1$-$C_{10}$ alkylene, and $R^2$ is unsubstituted isopropyl. In a still further related embodiment, $R^3$ is methyl, $R_3$ is hydrogen, and $L^1$ is methylene. In some embodiments, the compound is compound 76 of Table 1, below.

In some embodiments, $R^1$ is substituted or unsubstituted cycloalkyl, substituted or unsubstituted heterocycloalkyl, substituted or unsubstituted aryl, or substituted or unsubstituted heteroaryl.

$R^1$ may also be an unsubstituted $C_3$-$C_8$ cycloalkyl, unsubstituted 4 to 8 membered heterocycloalkyl, unsubstituted aryl, unsubstituted heteroaryl. Additionally, $R^1$ may be $C_3$-$C_8$ cycloalkyl, 4 to 8 membered heterocycloalkyl, aryl, or heteroaryl, that is substituted with a substituent selected from a halogen (e.g. fluorine and/or chlorine), hydroxyl, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl. In some embodiments, $R^1$ is substituted or unsubstituted aryl (e.g. phenyl), or substituted or unsubstituted heteroaryl (e.g. benzothiophenyl).

In some embodiments, $R^1$ is a substituted phenyl having the formula:

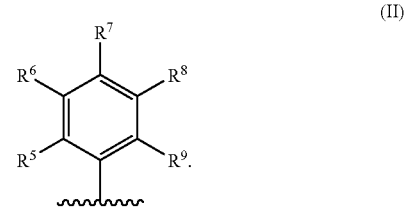

(II)

In addition to a substituted phenyl of Formula (II), $R^1$ may be a substituted or unsubstituted benzodioxolanyl, substituted or unsubstituted acenaphthenyl, substituted or unsubstituted naphthyl, substituted or unsubstituted benzothiophenyl, substituted or unsubstituted cyclopentyl, or substituted or unsubstituted thienyl. In a related embodiment, the substituted or unsubstituted naphthyl is a substituted or unsubstituted naphthalen-2-yl. Alternatively, the substituted or unsubstituted naphthyl may be a naphthalen-1-yl substituted with a substituent selected from a hydroxyl, sulfhydryl, cyano, nitro, substituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted thienyl, or unsubstituted cyclopentyl.

In some embodiments, the naphthalen-1-yl substituent is a hydroxyl, sulfhydryl, cyano, nitro, substituted $C_1$-$C_{20}$ alkyl, substituted or unsubstituted 2 to 20 membered heteroalkyl, substituted or unsubstituted $C_3$-$C_8$ cycloalkyl, substituted or unsubstituted 4 to 8 membered heterocycloalkyl, substituted or unsubstituted aryl, or substituted or unsubstituted heteroaryl; thienyl substituted with a substituted or unsubstituted alkyl; or unsubstituted cyclopentyl.

In other embodiments, $R^1$ is unsubstituted benzodioxolanyl or benzodioxolanyl substituted with a substituent selected from a halogen, hydroxyl, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl.

Alternatively, $R^1$ is unsubstituted acenaphthenyl or acenaphthenyl substituted with a substituent selected from a halogen, hydroxyl, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl.

$R^1$ may also be a unsubstituted naphthalen-2-yl or naphthalen-2-yl substituted with a substituent selected from a halogen, hydroxyl, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl.

In some embodiments, $R^1$ is naphthalen-1-yl substituted with a substituent selected from a hydroxyl, sulfhydryl, cyano, nitro, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl. The naphthalen-1-yl substituent may also be selected from $C_1$-$C_{10}$ alkyl, 2 to 10 membered heteroalkyl, $C_3$-$C_8$ cycloalkyl, 4 to 8 membered heterocycloalkyl, aryl, or heteroaryl, that is substituted with a substituent selected from a halogen, hydroxyl, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl.

In other embodiments, $R^1$ is thienyl substituted with an unsubstituted $C_1$-$C_{10}$ alkyl or a $C_1$-$C_{10}$ alkyl substituted with a substituent selected from a halogen, hydroxyl, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl.

$R^1$ may also be an unsubstituted cyclopentyl. Alternatively, $R^1$ is unsubstituted benzodioxolanyl or benzodioxolanyl substituted with a substituent selected from a halogen and unsubstituted $C_1$-$C_{10}$ alkyl; unsubstituted acenaphthenyl or acenaphthenyl substituted with a substituent selected from a halogen and unsubstituted $C_1$-$C_{10}$ alkyl; unsubstituted naphthalen-2-yl or naphthalen-2-yl substituted with a substituent selected from a halogen and unsubstituted $C_1$-$C_{10}$ alkyl; or thienyl substituted with an unsubstituted $C_1$-$C_{10}$ alkyl or a $C_1$-$C_{10}$ alkyl substituted with a substituent selected from a halogen and unsubstituted $C_1$-$C_{20}$ alkyl; or unsubstituted cyclopentyl. $R^1$ may additionally be a naphthalen-1-yl substituted with an unsubstituted 2 to 10 membered heteroalkyl; or $C_1$-$C_{10}$ alkyl, or 2 to 10 membered heteroalkyl substituted with a substituent selected from a halogen and unsubstituted $C_1$-$C_{20}$ alkyl.

In some embodiments, $R^1$ is unsubstituted benzodioxolanyl; unsubstituted acenaphthenyl; unsubstituted naphthalen-2-yl; naphthalen-2-yl substituted with a substituent selected from a halogen and unsubstituted $C_1$-$C_5$ alkyl; or thienyl substituted with an unsubstituted $C_1$-$C_5$ alkyl; or unsubstituted cyclopentyl. $R^1$ may additionally be naphthalen-1-yl substituted with an unsubstituted 2 to 5 membered heteroalkyl; or $C_1$-$C_5$ alkyl or 2 to 5 membered heteroalkyl, that is substituted with a halogen and unsubstituted $C_1$-$C_{20}$ alkyl.

In other embodiments, $R^1$ is unsubstituted benzodioxolanyl; unsubstituted acenaphthenyl; unsubstituted naphthalen-2-yl or naphthalen-2-yl substituted with a halogen; thienyl substituted with an unsubstituted $C_1$-$C_5$ alkyl; or unsubstituted cyclopentyl.

In some embodiments, $R^1$ is $R^{14}$-substituted $C_1$-$C_{20}$ alkyl, 2 to 20 membered unsubstituted heteroalkyl, substituted or unsubstituted cycloalkyl, substituted or unsubstituted heterocycloalkyl, $R^{15}$-substituted heteroaryl, substituted or unsubstituted fused-ring heteroaryl, or $R^{16}$-substituted aryl. $R^{14}$ is oxo, —OH, halogen, —$CF_3$, —$NH_2$, 2 to 20 membered substituted or unsubstituted heteroalkyl (e.g. alkoxy), 3 to 7 membered substituted or unsubstituted heterocycloalkyl, substituted or unsubstituted heteroaryl, or $R^{16}$-substituted aryl. $R^{15}$ is —OH, halogen, —$CF_3$, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{16}$ is substituted or unsubstituted cycloalkyl, substituted or unsubstituted heterocycloalkyl, substituted or unsubstituted heteroaryl, or substituted or unsubstituted aryl, or substituted or unsubstituted ortho-benzyloxy (i.e. o-benzyloxy). In some embodiments, if $R^1$ is not unsubstituted alkyl, then $R^1$ is optionally 2 to 20 membered substituted heteroalkyl.

In some embodiments, $R^1$ is substituted naphthyl. In some embodiments, $R^1$ is substituted or unsubstituted acenaphthenyl. In some embodiments, $R^1$ is substituted or unsubstituted thiophenyl-phenyl. In some embodiments, $R^1$ is substituted or unsubstituted naphthyl, or substituted thiophenyl, and $R^2$ is hydrogen or methyl.

In some embodiments, $R^2$ is a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ may be selected from a substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 4 to 8 membered heterocycloalkyl, substituted or unsubstituted aryl, and substituted or unsubstituted heteroaryl. In some embodiment, $R^2$ is not connected to the remainder of the molecule via nitrogen (i.e. a nitrogen-carbon bond). In some embodiments, $R^2$ is connected to the remainder of the molecule via a carbon-carbon bond.

Alternatively, $R^2$ is unsubstituted $C_1$-$C_{20}$ alkyl; unsubstituted 2 to 20 membered heteroalkyl; unsubstituted $C_3$-$C_8$ cycloalkyl; unsubstituted 4 to 8 membered heterocycloalkyl; unsubstituted aryl; unsubstituted heteroaryl; or $C_1$-$C_{20}$ alkyl, 2 to 20 membered heteroalkyl, $C_3$-$C_8$ cycloalkyl, 4 to 8 membered heterocycloalkyl, aryl, or heteroaryl, that is substituted with a substituent selected from a halogen, hydroxyl, sulfhydryl, cyano, oxy, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl.

In some embodiments, $R^2$ is an unsubstituted $C_1$-$C_{10}$ alkyl; unsubstituted 2 to 10 membered heteroalkyl; unsubstituted $C_5$ cycloalkyl; unsubstituted phenyl; unsubstituted benzyl; or $C_1$-$C_{10}$ alkyl, 2 to 10 membered heteroalkyl, $C_5$ cycloalkyl, phenyl, or benzyl, substituted with a substituent selected from a halogen, hydroxyl, oxy, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl.

In other embodiments, $R^2$ is unsubstituted $C_1$-$C_{10}$ alkyl; unsubstituted 2 to 10 membered heteroalkyl; unsubstituted $C_5$ cycloalkyl; unsubstituted phenyl; unsubstituted benzyl; or $C_1$-$C_{10}$ alkyl or 2 to 10 membered heteroalkyl, that is substituted with a substituent selected from a halogen, hydroxyl, and oxy.

Alternatively, $R^2$ is a hydrogen, unsubstituted alkyl, unsubstituted heteroalkyl, unsubstituted cycloalkyl, unsubstituted aryl, unsubstituted arylalkyl, or unsubstituted alkylesteryl. $R^2$ may also be an unsubstituted $C_1$-$C_{20}$ alkyl. In some embodiments, $R^2$ is an unsubstituted $C_1$-$C_{10}$ alkyl. In other embodiments, $R^2$ is tertiarybutyl.

In some embodiments, $R^2$ is $R^{10}$-substituted $C_1$-$C_{20}$ alkyl, 2 to 20 membered substituted or unsubstituted heteroalkyl, $R^{11}$-substituted $C_3$-$C_8$ cycloalkyl, $R^{11}$-substituted $C_3$-$C_8$ heterocycloalkyl, $R^{12}$-substituted heteroaryl, or $R^{13}$-substituted aryl. $R^{10}$ is oxo, —OH, halogen, —$CF_3$, —$NH_2$, 2 to 20 membered substituted or unsubstituted heteroalkyl (e.g. substituted or unsubstituted alkoxy), 3 to 7 membered substituted or unsubstituted heterocycloalkyl, substituted or unsubstituted heteroaryl, or $R^{13}$-substituted aryl. $R^{11}$ is oxo, —OH, halogen, —$CF_3$, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{12}$ is —OH, halogen, —$CF_3$, —$NH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{13}$ is —OH, —$NH_2$, substituted or unsubstituted cycloalkyl, substituted or unsubstituted heterocycloalkyl, substituted or unsubstituted heteroaryl, or substituted or unsubstituted aryl. In some related embodiments, if $R^3$ and $R^4$ are hydrogen and $R^1$ is 4-methylphenyl, then $R^2$ is not 2-ethylacetyl. In other related embodiments, if $R^3$ and $R^4$ are hydrogen and $R^1$ is methylphenyl or ethylphenyl, then $R^2$ is not alkylacetyl.

In certain embodiments, $R^3$ and $R^4$ are independently selected from a hydrogen, substituted or unsubstituted alkyl, and substituted or unsubstituted heteroalkyl. In some embodiments, $R^3$ and $R^4$ are, independently, a hydrogen, substituted or unsubstituted $C_1$-$C_{10}$ alkyl, or substituted or unsubstituted 2 to 10 membered heteroalkyl. $R^3$ and $R^4$ may also be independently selected from a hydrogen, unsubstituted $C_1$-$C_{10}$ alkyl, and unsubstituted 2 to 10 membered heteroalkyl. Alternatively, $R^3$ and $R^4$ are, independently, a hydrogen or methyl. In some embodiments, $R^3$ and $R^4$ are hydrogen.

In some embodiments, $R^3$ and $R^4$ are, independently, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^3$ and $R^4$ are unsubstituted alkyl.

In some embodiments, $R^1$ is phenyl substituted with halogen, methyl, —OH, —$CF_3$, —$OCH_3$, or —$NH_2$; $R^2$ is $C_1$-$C_{10}$ unsubstituted alkyl; $R^3$ and $R^4$ are independently hydrogen or methyl; and $L^1$ is methylene. $R^1$ may also be phenyl substituted with halogen (e.g. chlorine). In some embodiments, $R^1$ is ortho-chlorophenyl. $R^1$ may also be phenyl substituted with halogen, —OH, —$CF_3$, —$OCH_3$, or —$NH_2$. In some embodiments, $R^3$ and $R^4$ are hydrogen. In some embodiments, $R^3$ is hydrogen and $R^4$ is methyl.

$L^1$ may be a bond, unsubstituted $C_1$-$C_{10}$ alkylene, or $C_1$-$C_{10}$ alkylene substituted with unsubstituted alkyl, unsubstituted heteroalkyl, unsubstituted cycloalkyl, unsubstituted heteroalkyl, unsubstituted aryl, or unsubstituted heteroaryl. In some embodiments, $L^1$ is methylene.

$L^1$ may also be a bond, substituted or unsubstituted alkylene, or substituted or unsubstituted heteroalkylene, wherein if $R^1$ is a substituted phenyl, substituted or unsubstituted benzodioxolanyl, or substituted or unsubstituted cyclopentyl, then $L^1$ is substituted or unsubstituted alkylene, or substituted or unsubstituted heteroalkylene.

In some embodiments, $L^1$ is a bond or substituted or unsubstituted alkylene, wherein if $R^1$ is a substituted phenyl, substituted or unsubstituted benzodioxolanyl, or unsubstituted cyclopentyl, then $L^1$ is substituted or unsubstituted alkylene.

In other embodiments, $L^1$ is a bond or unsubstituted $C_1$-$C_{20}$ alkylene, wherein if $R^1$ is a phenyl, benzodioxolanyl, or cyclopentyl, then $L^1$ is an unsubstituted $C_1$-$C_{20}$ alkylene. In other embodiments, $L^1$ is a bond or unsubstituted $C_1$-$C_{20}$ alkylene, wherein if $R^1$ is a phenyl, benzodioxolanyl, or cyclopentyl, then $L^1$ is an unsubstituted $C_2$-$C_{20}$ alkylene. In other embodiments, $L^1$ is a bond or unsubstituted $C_1$-$C_{20}$ alkylene, wherein if $R^1$ is a phenyl, benzodioxolanyl, or cyclopentyl, then $L^1$ is an unsubstituted $C_3$-$C_{20}$ alkylene.

Alternatively, $L^1$ is a bond or unsubstituted $C_1$-$C_{10}$ alkylene, wherein if $R^1$ is a phenyl, benzodioxolanyl, or cyclopentyl, then $L^1$ is an unsubstituted $C_1$-$C_{10}$ alkylene.

$L^1$ may also be a bond or unsubstituted $C_1$-$C_5$ alkylene, wherein if $R^1$ is a phenyl, benzodioxolanyl, or cyclopentyl, then $L^1$ is an unsubstituted $C_1$-$C_5$ alkylene. Alternatively, $L^1$ may be a bond or methylene, wherein if $R^1$ is a phenyl, benzodioxolanyl, or cyclopentyl, then $L^1$ is a methylene.

In some embodiments, $L^1$ is substituted or unsubstituted [1,1]cycloalkylene, such as substituted or unsubstituted [1,1]-cyclopropylene. In some embodiments, $L^1$ is unsubstituted [1,1]cycloalkylene, such as unsubstituted [1,1]-cyclopropylene.

In an exemplary embodiment, $R^5$, $R^6$, $R^7$, $R^8$ and $R^9$ of Formula (II), above, are independently selected from a hydrogen; halogen; hydroxyl; sulfhydryl; cyano; nitro; substituted or unsubstituted alkyl; substituted or unsubstituted heteroalkyl; substituted or unsubstituted cycloalkyl; substituted or unsubstituted heterocycloalkyl; substituted or unsubstituted aryl; and substituted or unsubstituted heteroaryl.

In some embodiments, $R^5$, $R^7$, and $R^9$ are independently selected from a hydrogen; halogen; hydroxyl; sulfhydryl; cyano; nitro; substituted or unsubstituted alkyl; substituted or unsubstituted heteroalkyl; substituted or unsubstituted cycloalkyl; substituted or unsubstituted heterocycloalkyl; substituted or unsubstituted aryl; and substituted or unsubstituted heteroaryl. $R^6$ and $R^8$ are independently selected from a hydrogen, halogen, hydroxyl, sulfhydryl, cyano, nitro, substituted or unsubstituted alkyl, unsubstituted heteroalkyl, substituted or unsubstituted cycloalkyl, substituted or unsubstituted heterocycloalkyl, substituted or unsubstituted aryl, substituted or unsubstituted heteroaryl, and heteroalkyl substituted with a substituted aryl. In certain embodiments, $R^5$, $R^6$, $R^8$, and $R^9$ are not simultaneously hydrogen.

In other embodiments, $R^5$, $R^7$, and $R^9$ are, independently, hydrogen, halogen, hydroxyl, sulfhydryl, cyano, nitro, substituted or unsubstituted $C_1$-$C_{20}$ alkyl, substituted or unsubstituted 2 to 20 membered heteroalkyl, substituted or unsubstituted $C_3$-$C_8$ cycloalkyl, substituted or unsubstituted 4 to 8 membered heterocycloalkyl, substituted or unsubstituted aryl, or substituted or unsubstituted heteroaryl.

Alternatively, $R^5$, $R^7$, and $R^9$ are, independently, hydrogen; halogen; hydroxyl; sulfhydryl; cyano; nitro; unsubstituted $C_1$-$C_{10}$ alkyl; unsubstituted 2 to 10 membered heteroalkyl; unsubstituted $C_3$-$C_8$ cycloalkyl; unsubstituted 4 to 8 membered heterocycloalkyl; unsubstituted aryl; unsubstituted heteroaryl; or $C_1$-$C_{10}$ alkyl, 2 to 20 membered heteroalkyl, $C_3$-$C_8$ cycloalkyl, 4 to 8 membered heterocycloalkyl, aryl, or heteroaryl, that is substituted with a substituent selected from a halogen, hydroxyl, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted heteroaryl, unsubstituted aryl, and aryl substituted with a halogen or unsubstituted heteroaryl.

$R^5$, $R^7$, and $R^9$ may also be, independently, hydrogen; halogen; hydroxyl; unsubstituted $C_1$-$C_{10}$ alkyl; unsubstituted 2 to 10 membered heteroalkyl; unsubstituted $C_5$-$C_8$ cycloalkyl; unsubstituted 5 to 8 membered heterocycloalkyl; unsubstituted aryl; unsubstituted heteroaryl; or $C_1$-$C_{10}$ alkyl or 2 to 10 membered heteroalkyl, that is substituted with a substituent selected from an unsubstituted aryl, unsubstituted heteroaryl, and aryl substituted with a halogen.

In another embodiment, $R^5$, $R^7$, and $R^9$ are independently selected from a hydrogen, halogen, unsubstituted $C_1$-$C_{10}$ alkyl, and unsubstituted 2 to 10 membered heteroalkyl. $R^5$, $R^7$, and $R^9$ may also independently be a hydrogen, halogen, methyl, or methoxy.

In another embodiment, $R^6$ and $R^8$ are, independently, hydrogen, halogen, hydroxyl, sulfhydryl, cyano, nitro, substituted or unsubstituted $C_1$-$C_{20}$ alkyl, unsubstituted 2 to 20 membered heteroalkyl, substituted or unsubstituted $C_3$-$C_8$ cycloalkyl, substituted or unsubstituted 4 to 8 membered heterocycloalkyl, substituted or unsubstituted aryl, substituted or unsubstituted heteroaryl, or 2 to 20 membered heteroalkyl substituted with a substituted aryl.

In some embodiments, $R^6$ and $R^8$ are, independently, hydrogen; halogen; hydroxyl; sulfhydryl; cyano; nitro; unsubstituted $C_1$-$C_{10}$ alkyl; unsubstituted 2 to 10 membered heteroalkyl; unsubstituted $C_3$-$C_8$ cycloalkyl; unsubstituted 4 to 8 membered heterocycloalkyl; unsubstituted aryl; unsubstituted heteroaryl; 2 to 10 membered heteroalkyl substituted with a substituted aryl; or $C_1$-$C_{10}$ alkyl, $C_3$-$C_8$ cycloalkyl, 4 to 8 membered heterocycloalkyl, aryl, or heteroaryl, substituted with a substituent selected from a halogen, hydroxyl, sulfhydryl, cyano, nitro, unsubstituted $C_1$-$C_{10}$ alkyl, unsubstituted 2 to 10 membered heteroalkyl, unsubstituted $C_3$-$C_8$ cycloalkyl, unsubstituted 4 to 8 membered heterocycloalkyl, unsubstituted aryl, and unsubstituted heteroaryl.

In other embodiments, $R^6$ and $R^8$ are, independently, hydrogen; halogen; hydroxyl; unsubstituted $C_1$-$C_{10}$ alkyl; unsubstituted 2 to 10 membered heteroalkyl; unsubstituted $C_3$-$C_8$ cycloalkyl; unsubstituted 4 to 8 membered heterocycloalkyl; unsubstituted aryl; unsubstituted heteroaryl; 2 to 10 membered heteroalkyl substituted with a haloaryl; or $C_1$-$C_{10}$ alkyl substituted with a substituent selected from an unsubstituted aryl, haloalkyl, or unsubstituted heteroaryl.

$R^6$ and $R^8$ may also be selected from a hydrogen, halogen, unsubstituted $C_1$-$C_{10}$ alkyl, unsubstituted 2 to 10 membered heteroalkyl, or 2 to 5 membered heteroalkyl substituted with a haloaryl.

Alternatively, $R^6$ and $R^8$ are independently selected from a hydrogen, halogen, methyl, methoxy, and methoxy substituted with a haloaryl.

In some embodiments, each substituted group described above in the compounds of Formulae (I) and/or (II) is substituted with at least one substituent group. Fore example, in some embodiments, each substituted alkyl, substituted heteroalkyl, substituted cycloalkyl, substituted heterocycloalkyl, substituted aryl, substituted heteroaryl, substituted alkylene, substituted cycloalkylene, and/or substituted heteroalkylene, described above in the compounds of Formulae (I) and/or (II) are substituted with at least one substituent group. In other embodiments, at least one or all of these groups are substituted with at least one size-limited substituent group. Alternatively, at least one or all of these groups are substituted with at least one lower substituent group.

In other embodiments of the compounds of Formulae (I) and/or (II), each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 4 to 8 membered heterocycloalkyl, each substituted or unsubstituted alkylene is a substituted or unsubstituted $C_1$-$C_{20}$ alkylene, each substituted or unsubstituted cycloalkylene is a $C_3$-$C_8$ cycloalkylene, and/or each substituted or unsubstituted heteroalkylene is a substituted or unsubstituted 2 to 20 membered heteroalkylene.

Alternatively, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, each substituted or unsubstituted heterocycloalkyl is a substituted or unsubstituted 5 to 7 membered heterocycloalkyl, each substituted or unsubstituted alkylene is a substituted or unsubstituted $C_1$-$C_8$ alkylene, each substituted or unsubstituted cycloalkylene is a $C_3$-$C_6$ cycloalkylene, and/or each substituted or unsubstituted heteroalkylene is a substituted or unsubstituted 2 to 8 membered heteroalkylene.

In some embodiments, the compounds of the invention are the subset of compounds set forth in Table 1 below, with the exception of compound 13 and/or compound 57. Although compound 57 does not fall within the scope of Formula (I), in some embodiments compound 57 of Table 1 is useful in the methods of the present invention. In some embodiments, the compounds of the invention are the subset of compounds set forth in Table 1 below, with the exception of compound 57. In some embodiments, the compounds of the invention are the subset of compounds in Table 1 that are set forth as "active." In some embodiments, the compounds of the invention do not include those compounds set forth in Table 2 below. One skilled in the art, using the methods described herein and/or methods well known in the art, can easily determine which compounds are useful as anti-inflammatory compounds (see e.g. section III below).

II. Exemplary Synthesis

The compounds of the invention are synthesized by an appropriate combination of generally well known synthetic methods. Techniques useful in synthesizing the compounds of the invention are both readily apparent and accessible to those of skill in the relevant art in view of the disclosure herein. The discussion below is offered to illustrate certain of the diverse methods available for use in assembling the compounds of the invention. However, the discussion is not intended to define the scope of reactions or reaction sequences that are useful in preparing the compounds of the present invention.

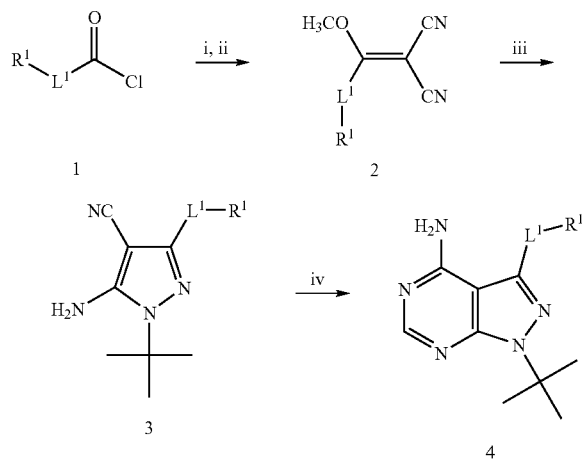

Scheme 1

1, 2, 3, 4

In scheme 1, $R^1$ and $L^1$ are as defined above. In step (i), carbonyl compound 1 is reacted with NaH and malononitrile in THF, followed by (ii) treatment with NaHCO$_3$, and dimethyl sulfate in dioxane/H$_2$O to form the corresponding alkene 2. Cyclization of 2 is accomplished by refluxing in the presence of triethylamine and tertbutylhydrazine hydrochloride in ethanol to from the pyrazole 3. Finally, 3 is reacted with formamide to yield the pyrazolopyrimidine 4.

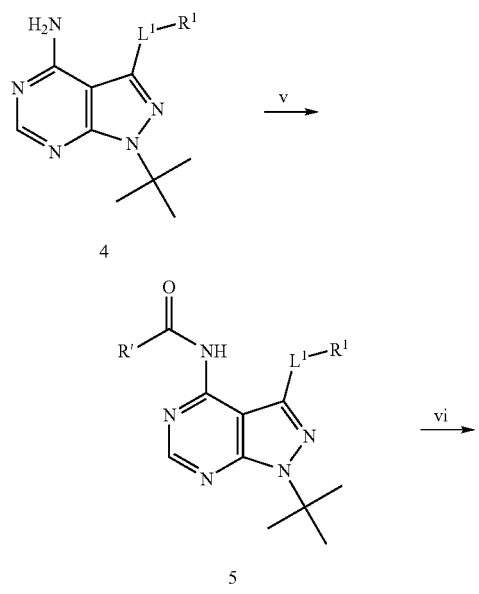

Scheme 2

4, 5

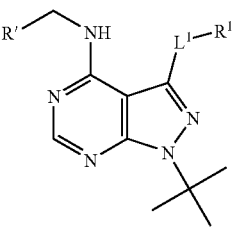

6

The amine substituent of 4 may be derivatized by reacting with the appropriate acyl chloride (R'—C(O)—Cl) in the presence of pyridine (v) (Scheme 2). The resulting amide may be reduced by refluxing with LiAlH$_4$ in dry tetrahydrofuran to form 6. In scheme 2, R' represents substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In some embodiments, the —CH$_2$—R' moiety is $R^3$, which is defined above.

For a more detailed discussion of useful synthesis procedures, see Bishop et al., *J. Am. Chem. Soc.* 121, 627-631 (1999) and Bishop et al., *Current Biology*, 8: 257-266 (1998).

III. Methods of Identifying an Anti-Inflammatory Pyrazolopyrimidine

In another aspect, the present invention provides a method for identifying anti-inflammatory pyrazolopyrimidine compounds. The method includes contacting a candidate anti-inflammatory pyrazolopyrimidine compound with a cell culture assay. The cell culture assay may include more than one type of cell, also referred to herein as a cell culture assay combination. The cell culture assay combination may include, for example and without limitation, human endothelial cells in an inflammatory state with or without peripheral blood mononuclear cells. In one type of cell culture assay, changes in the expression of at least two different gene products relevant to an inflammatory state are detected. The change in the expression of the at least two different gene products is compared to the expression of those gene products in the absence of the candidate anti-inflammatory pyrazolopyrimidine compound, and if the candidate compound alters the expression of one or more of such gene products in a manner consistent with anti-inflammatory action (for example, by decreasing the expression of a gene product that induces an inflammatory state or is characteristic of an inflammatory state or by increasing the expression of a gene product that inhibits inflammation), then the candidate compound is thereby identified as an anti-inflammatory pyrazolopyrimidine compound. Cell culture assays and methods for analyzing the data obtained by them useful in this aspect of the invention are described in PCT publication Nos. 05/023987; 04/094992; 04/094609; 04/022711; 03/023753; and 01/067103; and U.S. Pat. Nos. 6,656,695; and 6,763,307, each of which is incorporated herein by reference.

In some embodiments, the gene products analyzed are the products of a gene selected from E-selectin, ICAM-1, VCAM-1, CXLC9/MIG, IL-6, CXCL8/IL-8, HLA-DR, CCL2/MCP-1, P-selectin, VEGFR2, CD87/uPAR, CD55, CCL26/Eotaxin-3, CD14, CD40, CD69, CD31, CD38, CD142/TF, IL-1α, M-CSF, CD141/TM, Endothelin-1, LDLR, CXCL10/IP-10, CD3, and IL-2. Additional gene products that may be analyzed in such assays are discussed in detail, for example, in the above cited PCT patent publications and issued U.S. patents, each of which has been incorporated by reference in their entirety for all purposes. Other exemplary targets and pathways that may be detected in such cell culture assays are illustrated in FIGS. 1A and 1B below.

The inflammatory state of the cells in the cell culture assay may be achieved by adding to the culture one or more inflammatory factors selected from TNF-α, TNF-β, IL-1, IL-2, IL-4, IL-12, IL-13, Staphylococcal Enterotoxin B (SEB), Staphylococcal Enterotoxin E (SEE), toxic shock syndrome toxin (TSST), lipopolysaccharide (LPS), anti-CD3 antibody, anti-T cell receptor antibody, histamine and IFN-γ. The inflammatory factors are typically added in an amount and for a time sufficient to induce said inflammatory state. In some embodiments, at least one, two or three inflammatory factors are added. Additional inflammatory factors are discussed in detail, for example, in the above cited PCT patent publications and issued U.S. patents.

In certain embodiments, activities of a candidate pyrazolopyrimidine compound are compared to a known anti-inflammatory compound. Pyrazolopyrimidine compounds with novel activity profiles or with activity profiles similar to other anti-inflammatory compounds may thereby be detected.

In an exemplary embodiment, a Biologically Multiplexed Activity Profiling system, known under the mark BioMAP™ system, is employed. Useful BioMAP systems are discussed in detail, for example, in the above cited PCT patent publications and issued U.S. patents and in Kunkel et al., *ASSAY and Drug Development Technologies,* 2: 431-441 (2004), incorporated herein by reference.

Methods for selecting cells and culture conditions for screening candidate anti-inflammatory pyrazolopyrimidines, identification of an optimized set of discrete parameters to be measured, the use of BioMAP analysis for rapid identification and characterization of candidates, and the like, are within the skill of those having knowledge in the biological and/or biochemical arts in view of the disclosure herein and that of the above cited PCT patent publications and issued U.S. patents. In some embodiments, a large number of cellular pathways, and the rapid identification of compounds that cause cellular responses, are simultaneously screened.

Agents are screened for biological activity by adding an agent to be screened to at least one and usually a plurality of assay combinations to form a panel of assay combinations, usually in conjunction with assay combinations lacking agent. The change in parameter readout in response to agent is measured, desirably normalized, and the resulting BioMAP readout may then be evaluated by comparison to reference BioMAP readouts. The reference BioMAP readouts may include basal readouts in the presence and absence of the factors, BioMAP readouts obtained with other agents, which may or may not include known inhibitors of known pathways. Agents of interest for analysis include any biologically active molecule with the capability of modulating, directly or indirectly, the phenotype of interest of a cell of interest.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.,* 17(12):477-81). Thus, antibodies can be genetically modified to provide a fluorescent dye as part of their structure. Applicable methods are generally known in art, and are discussed in detail, for example, in the above cited PCT patent publications and issued U.S. patents.

In certain embodiments, human umbilical vein endothelial cells (HUVEC) and/or peripheral blood mononuclear cells (PBMC) are contacted with different combinations of cytokines to induce an inflammatory response. Exemplary cytokine combinations are illustrated in FIG. 1B. The inflammatory response is assessed by detecting the presence of the gene products shown in FIG. 1B.

IV. Methods for Treating or Preventing a Disorder Characterized by Inflammation

In another aspect, the present invention provides a method for treating or preventing a disorder characterized by inflammation, said method including administering to a subject a therapeutically effective amount of a compound of the present invention.

In certain embodiments, the inflammatory process that occurs in response to or is an underlying cause of infection, trauma, autoimmune disease, cardiovascular disease, neoplasia, hyperplasia, addiction, infection, obesity, cellular degeneration, apoptosis, or senescence, or differentiation.

The disorder may be selected from the group consisting of vasculitis, multiple sclerosis, diabetes, inflammatory bowel disease (e.g. Crohn's disease and ulcerative colitis), psoriasis, arthritis (e.g. rheumatoid arthritis, spondyloarthopathies, gouty arthritis, osteoarthritis, and juvenile arthritis), asthma, stroke, atherosclerosis (including atherosclerotic plaque rupture), restenosis, and lupus (including systemic lupus erythematosus).

Other disorders associated with abnormal inflammation include, for example, headaches (e.g. migraine headaches), bronchitis, menstrual cramps, tendonitis, gastritis, vascular diseases, uveitis, Sjogren's disease, sclerodoma, nephrotic syndrome, swelling occurring after injury, myocardial ischemia, fever (including rheumatic fever and fever associated with influenza and other viral infections), common cold, dysmenorrhea, emphysema, acute respiratory distress syndrome, chronic obstructive pulmonary disease, Alzheimer's disease, organ transplant toxicity, cachexia, allergic reactions, allergic contact hypersensitivity, cancer (such as solid tumor cancer including colon cancer, breast cancer, lung cancer and prostrate cancer; hematopoietic malignancies including leukemias and lymphomas; Hodgkin's disease; aplastic anemia, skin cancer and familiar adenomatous polyposis), tissue ulceration, peptic ulcers, regional enteritis, ulcerative colitis, diverticulitis, recurrent gastrointestinal lesion, gastrointestinal bleeding, coagulation, synovitis, gout, ankylosing spondylitis, restenosis, periodontal disease, epidermolysis bullosa, osteoporosis, loosening of artificial joint implants, aortic aneurysm (including abdominal aortic aneurysm and brain aortic aneurysm), periarteritis nodosa, congestive heart failure, myocardial infarction, cerebral ischemia, head trauma, spinal cord injury, neuralgia, neurodegenerative disorders (acute and chronic), autoimmune disorders, Huntington's disease, Parkinson's disease, migraine, depression, peripheral neuropathy, pain (including low back and neck pain, headache and toothache), gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders (such as psoriasis, eczema, scleroderma and dermatitis), myasthenia gravis, polymyositis, myositis, bursitis, burns, diabetes (including types I and II diabetes, diabetic retinopathy, neuropathy and nephropathy, insulin dependent diabetes mellitus (IDDM)), tumor invasion, tumor growth, tumor metastasis, corneal scarring, scleritis, immunodeficiency diseases (such as AIDS in humans and FLV, FIV in cats), sepsis, premature labor, hypoprothrombinemia, hemophilia, thyroiditis, sarcoidosis, Behcet's syndrome, hypersensitivity, kidney disease, Rickettsial infections (such as Lyme disease, Erlichiosis), Protozoan diseases (such as malaria, giardia, coccidia), reproductive disorders (preferably in livestock) and septic shock.

Treatment may be conducted in a mammal (e.g. a human, cat, dog, or livestock), and the treatment method comprises administering a therapeutically effective amount of a compound of Formula (I) or a pharmaceutically acceptable salt thereof in combination with a pharmaceutically acceptable carrier.

V. Anti-Inflammatory Activity

As discussed above, the present invention provides anti-inflammatory compounds useful in the treatment of diseases and conditions in which inflammation is involved in disease progression or the manifestation of symptoms of the disease or condition.

In one embodiment, the compounds of the invention are the subset of compounds of Formula (I) that are T cell activation inhibitors. T-cell activation inhibitors are those compounds that strongly inhibit T cell activation in a cell-based assay (e.g. a BioMAP assay as described above, where, for example, a superantigen is used to stimulate T cells). The phrase "strongly inhibit T cell activation," as used herein, refers to compounds that inhibit the expression of at least one gene product selected from E-selectin, ICAM-1, VCAM-1, CXLC9/MIG, CXCL8/IL-8, CCL2/MCP-1, CD87/uPAR, CCL26/Eotaxin-3, CD40, CD69, CD38, CD142/TF, CXCL10/IP-10, or IL-2 by at least 50% in a cell-based assay. T-cell activation inhibitors may be especially useful in treating the inflammation underlying arthritis, psoriasis, vasculitis, multiple sclerosis, IBD, asthma, atherosclerosis, or other inflammatory disease. Illustrative pyrazolopyrimidine T cell activation inhibitor compounds of this embodiment include compounds 10, 13, 15, 17, 41, 48, and 54 in Table 1 below.

In another embodiment, the compounds of the invention are the subset of compounds of Formula (I0 that are monocyte activation and recruitment inhibitors. Monocyte activation inhibitors weakly inhibit T cell activation, strongly inhibit monocyte activation, and strongly inhibit MCP-1 and IL-8 production from multiple cell types including but not limited to endothelial cells, fibroblasts, and smooth muscle cells. The phrase "weakly inhibit T cell activation," as used herein, refers to compounds that inhibit the expression of at least one gene product selected from E-selectin, ICAM-1, VCAM-1, CXLC9/MIG, CXCL8/IL-8, CCL2/MCP-1, CD87/uPAR, CCL26/Eotaxin-3, CD40, CD69, CD38, CD142/TF, CXCL10/IP-10, or IL-2 by less than 50% in a cell-based assay. The phrase "strongly inhibit monocyte activation," as used herein, refers to compounds that inhibit the expression of at least one gene product selected from E-selectin, ICAM-1, VCAM-1, CXLC9/MIG, IL-6, CXCL8/IL-8, CCL2/MCP-1, CD14, CD40, CD69, CD142/TF, IL-1α, M-CSF, CD141/TM, or CXCL10/IP-10 by at least 50% in a cell-based assay. The phrase "strongly inhibit strongly inhibit MCP-1," as used herein, refers to compounds that inhibit the expression of MCP-1 gene product by at least 50% in a cell-based assay. The phrase "strongly inhibit strongly inhibit IL-8," as used herein, refers to compounds that inhibit the expression of IL-8 gene product by at least 50% in a cell-based assay. Monocyte activation inhibitors may be especially useful in treating the inflammation underlying multiple diseases including rheumatoid arthritis, ankylosing spondylitis, psoriatic arthritis, multiple sclerosis, psoriasis, inflammatory bowel disease, atherosclerosis, diabetes, lupus nephritis, and vasculitis. Illustrative pyrazolopyrimidine monocyte activation inhibitor compounds of this embodiment include compounds 30, 31, 36, 59, 62, 63, 64, 65, 72, and 76 in Table 1 below.

In another embodiment, the compounds of the invention are the subset of compounds of Formula (I) that are gamma interferon signaling inhibitors. Gamma interferon signaling inhibitors weakly inhibit T cell activation (see above) and monocyte activation (see above) but inhibit IFN-gamma signaling and collagen production. The phrase "weakly inhibit monocyte activation," as used herein, refers to compounds that inhibit the expression of at least one gene product selected from E-selectin, ICAM-1, VCAM-1, CXLC9/MIG, IL-6, CXCL8/IL-8, CCL2/MCP-1, CD14, CD40, CD69, CD142/TF, IL-1α, M-CSF, CD141/TM, or CXCL10/IP-10 by less than 50% in a cell-based assay. Gamma interferon signaling inhibitors may be especially useful in treating the inflammation underlying multiple diseases including rheumatoid arthritis, systemic sclerosis, COPD, asthma, atherosclerosis, cirrhosis, pulmonary fibrosis, sarcoidosis, keloids, and renal fibrosis. Illustrative pyrazolopyrimidine interferon gamma signaling inhibitor compounds of this embodiment include compounds 7, 8, 9, 11, 12, and 19 in Table 1 below.

VI. Pharmaceutical Compositions

In another aspect, the present invention provides pharmaceutical compositions comprising a pharmaceutically acceptable excipient and a compound of the present invention, such as a compound within the scope of Formula (I) provided above.

The compounds of the present invention can be prepared and administered in a wide variety of oral, parenteral and topical dosage forms. Oral preparations include tablets, pills, powder, dragees, capsules, liquids, lozenges, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The anti-inflammatory pyrazolopyrimidines of this invention can also be administered by intraocular, intravaginal, and intrarectal routes including via suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995). Accordingly, the present invention also provides pharmaceutical compositions comprising a pharmaceutically acceptable carrier or excipient and either a compound of Formula (I), or a pharmaceutically acceptable salt of a compound of Formula (I).

The compounds of the present invention may also be administered using an anti-inflammatory pyrazolopyrimidine coated stent. The stent may be inserted into a vessel, acting as a scaffold to provide structural support for the vessel thereby holding the vessel open and improving blood flow through the vessel. An anti-inflammatory pyrazolopyrimidine coated stent refers to a stent that has been coated with anti-inflammatory pyrazolopyrimidine and optionally additional agents, such as an appropriate pharmaceutical excipient. The anti-inflammatory pyrazolopyrimidine coated stent typically allows the anti-inflammatory pyrazolopyrimidine to be released over time into surrounding tissue. One skilled in the art understands that the stent may be adsorbed to, impregnated with, covalently attached to, or ionically bonded to the anti-inflammatory pyrazolopyrimidine.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, active component is mixed with a carrier having the necessary binding properties in suitable proportions and compacted in the shape and size desired.

The powders and tablets preferably contain from 5% or 10% to 70% of active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of active compound with encapsulating material as a carrier providing a capsule in which active component with or without other carriers, is surrounded by a carrier, which is thus in association with it. Similarly, cachets and lozenges are included within the pharmaceutical formulations of the invention. Tablets, powders, capsules, pills, cachets, and lozenges can be used as solid dosage forms suitable for oral administration.

Suitable solid excipients are carbohydrate or protein fillers and include, but are not limited to, sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain an anti-inflammatory pyrazolopyrimidine mixed with a filler or binders such as lactose or starches, lubricants such as talc or magnesium stearate, and, optionally, stabilizers. In soft capsules, the anti-inflammatory pyrazolopyrimidines may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). Aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to active component, colorants, flavors, stabilizers, buffers, artificial and natural sweeteners, dispersants, thickeners, solubilizing agents, and the like.

Oil suspensions can be formulated by suspending an anti-inflammatory pyrazolopyrimidine in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The anti-inflammatory pyrazolopyrimidines of the invention can be delivered transdermally, by a topical route, formulated as applicator sticks, solutions, suspensions, emulsions, gels, creams, ointments, pastes, jellies, paints, powders, and aerosols.

The anti-inflammatory pyrazolopyrimidines of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes can in some instances afford constant or near constant rates of delivery of the active agents for weeks or months.

The anti-inflammatory pyrazolopyrmidine pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the anti-inflammatory pyrazolopyrimidine formulations of the invention are used for parenteral administration, such as intravenous (IV) administration or administration into a body cavity or lumen of an organ. The formulations for administration will commonly comprise a solution of the anti-inflammatory pyrazolopyrimidine dissolved in a pharmaceutically acceptable carrier. Among acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known (for other compounds) sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of anti-inflammatory pyrazolopyrimidine in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the anti-inflammatory pyrazolopyrimidine formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the anti-inflammatory pyrazolopyrimidine into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of active component. The composition can, if desired, also contain other compatible therapeutic agents.

VII. Therapeutic Combinations

One of ordinary skill in art will appreciate that the compounds of the invention are useful in treating a diverse array of diseases. One of ordinary skill in art will also appreciate that, when using the compounds of the invention in the treatment of a specific disease, the compounds of the invention may be combined or otherwise co-administered with various existing therapeutic agents used for that disease. For example, for the treatment of rheumatoid arthritis, the compounds of the invention may be combined or co-administered with agents such as TNF-α inhibitors such as anti-TNF monoclonal antibodies and TNF receptor immunoglobulin molecules (such as Enbrel®), low dose methotrexate, lefunimide, hydroxychloroquine, d-penicilamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAIDs) such as piroxicam, diclofenac, propionic acids such as naproxen, flurbiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib and rofecoxib, analgesics and intraarticular therapies such as corticosteroids and hyaluronic acids such as hyalgan and synvisc.

Active ingredient (i.e. the compounds of Formula (I)) of the present invention may be administered in combination with inhibitors of other mediators of inflammation, comprising one or more members selected from the group consisting essentially of the classes of such inhibitors and examples thereof which include, matrix metalloproteinase inhibitors, aggrecanase inhibitors, TACE inhibitors, leukotriene receptor antagonists, IL-1 processing and release inhibitors, IL-1RA, H$_1$-receptor antagonists; kinin-B$_1$- and B$_1$-receptor antagonists; prostaglandin inhibitors such as PGD-, PGF-PGI$_2$-, and PGE-receptor antagonists; thromboxane A$_2$(TXA2-) inhibitors; 5- and 12-lipoxygenase inhibitors; leukotriene LTC$_4$-, LTD$_4$/LTE$_4$-, and LTB$_4$-inhibitors; PAF-receptor antagonists; gold in the form of an aurothio group together with various hydrophilic groups; immunosuppressive agents, e.g., cyclosporine, azathioprine, and methotrexate; anti-inflammatory glucocorticoids; penicillamine; hydroxychloroquine; anti-gout agents, e.g., colchicine, xanthine oxidase inhibitors, e.g., allopurinol, and uricosuric agents, e.g., probenecid, sulfinpyrazone, and benzbromarone.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, and antimetabolites such as methotrexate.

The compounds of the present invention may also be used in combination with anti-hypertensives and other cardiovascular drugs intended to offset the consequences of atherosclerosis, including hypertension, myocardial ischemia including angina, congestive heart failure, and myocardial infarction, selected from vasodilators such as hydralazine, β-adrenergic receptor antagonists such as propranolol, calcium channel blockers such as nifedipine, α$_2$-adrenergic agonists such as clonidine, α-adrenergic receptor antagonists such as prazosin, and HMG-CoA-reductase inhibitors (anti-hypercholesterolemics) such as lovastatin or atorvastatin.

Active ingredient of the present invention may also be administered in combination with one or more antibiotic, antifungal, antiprotozoal, antiviral or similar therapeutic agents.

The compounds of the present invention may also be used in combination with CNS agents such as antidepressants (such as sertraline), anti-Parkinsonian drugs (such as L-dopa, requip, mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metrifonate.

The compounds of the present invention may also be used in combination with osteoporosis agents such as roloxifene, lasofoxifene, droloxifene or fosomax and immunosuppressant agents such as FK-506 and rapamycin.

The present invention also relates to the formulation of active agents of the present invention alone or with one or more other therapeutic agents which are to form the intended combination, including wherein said different drugs have varying half-lives, by creating controlled-release forms of said drugs with different release times which achieves relatively uniform dosing; or, in the case of non-human patients, a medicated feed dosage form in which said drugs used in the combination are present together in admixture in said feed composition. There is further provided in accordance with the present invention co-administration in which the combination of drugs is achieved by the simultaneous administration of said drugs to be given in combination; including co-administration by means of different dosage forms and routes of administration; the use of combinations in accordance with different but regular and continuous dosing schedules whereby desired plasma levels of said drugs involved are maintained in the patient being treated, even though the individual drugs making up said combination are not being administered to said patient simultaneously.

This invention also relates to a method of or a pharmaceutical composition for treating inflammatory processes and diseases comprising administering a compound of this invention or its salt to a mammal including a human, cat, livestock or dog (preferably a dog), wherein said inflammatory processes and diseases are defined as above, and said inhibitory compound is used in combination with one or more other therapeutically active agents under the following conditions:

A.) where a joint has become seriously inflamed as well as infected at the same time by bacteria, fungi, protozoa, and/or virus, said inhibitory compound is administered in combination with one or more antibiotic, antifungal, antiprotozoal, and/or antiviral therapeutic agents;

B.) where a multi-fold treatment of pain and inflammation is desired, said inhibitory compound is administered in combination with inhibitors of other mediators of inflammation, comprising one or more members independently selected from the group consisting essentially of:
 (1) NSAID's;
 (2) H$_4$-receptor antagonists;
 (3) kinin-B$_4$- and B$_4$-receptor antagonists;
 (4) prostaglandin inhibitors selected from the group consisting of PGD-, PGF-PGI$_2$-, and PGE-receptor antagonists;
 (5) thromboxane A$_2$ (TXA$_2$-) inhibitors;
 (6) 5-, 12- and 15-lipoxygenase inhibitors;
 (7) leukotriene LTC$_4$-, LTD$_4$/LTE$_4$-, and LTB$_4$-inhibitors;
 (8) PAF-receptor antagonists;
 (9) gold in the form of an aurothio group together with one or more hydrophilic groups;
 (10) immunosuppressive agents selected from the group consisting of cyclosporine, azathioprine, and methotrexate;
 (11) anti-inflammatory glucocorticoids;
 (12) penicillamine;
 (13) hydroxychloroquine;
 (14) anti-gout agents including colchicine; xanthine oxidase inhibitors including allopurinol; and uricosuric agents selected from probenecid, sulfinpyrazone, and benzbromarone;

C.) where older mammals are being treated for disease conditions, syndromes and symptoms found in geriatric mammals, said inhibitory compound is administered in combination with one or more members independently selected from the group consisting essentially of:
 (1) cognitive therapeutics to counteract memory loss and impairment;
 (2) anti-hypertensives and other cardiovascular drugs intended to offset the consequences of atherosclerosis, hypertension, myocardial ischemia, angina, congestive heart failure, and myocardial infarction, selected from the group consisting of:
  a. diuretics;
  b. vasodilators;
  c. β-adrenergic receptor antagonists;
  d. angiotensin-II converting enzyme inhibitors (ACE-inhibitors), alone or optionally together with neutral endopeptidase inhibitors;
  e. angiotensin II receptor antagonists;
  f. renin inhibitors;
  g. calcium channel blockers;
  h. sympatholytic agents;
  i. α$_2$-adrenergic agonists;

j. α-adrenergic receptor antagonists; and
k. HMG-CoA-reductase inhibitors (anti-hypercholesterolemics);

(3) antineoplastic agents selected from antimitotic drugs such as the vinca alkaloids including but not limited to vinblastine and vincristine;

(4) growth hormone secretagogues;

(5) strong analgesics;

(6) local and systemic anesthetics; and (7) $H_2$-receptor antagonists, proton pump inhibitors, and other gastroprotective agents.

The term "treating", as used herein, refers to reversing, alleviating, inhibiting the progress of, or preventing the disorder or condition to which such term applies, or one or more symptoms of such disorder or condition. The term "treatment", as used herein, refers to act of treating, as "treating" is defined immediately above.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the anti-inflammatory compounds of the present invention are equally applicable to the methods of treating disease states and/or the pharmaceutical compositions described herein. All publications, patents, and patent applications cited herein are hereby incorporated by reference in their entirety for all purposes.

EXAMPLES

Example 1

Various pyrazolopyrimidine compounds were tested for anti-inflammatory properties using the methods detailed below.

Cytokines, Antibodies, and Reagents

Recombinant human interferon-γ (IFN-γ), TNF-α interleukin (IL)-1β, and IL-4 were from R&D Systems (Minneapolis, Minn.). Histamine was from Sigma (St. Louis, Mo.). Mouse antibodies were obtained from commercial sources: murine IgG and anti-human vascular endothelial growth factor receptor-2 (VEGFR2) (mIgG1; Sigma), anti-human tissue factor (mIgG1; Calbiochem, San Diego, Calif.), anti-human intercellular adhesion molecule-1 (ICAM-1) (mIgG1; Beckman Coulter, Fullerton, Calif.), and anti-human E-selectin (mIgG1; HyCult Biotechnology, Uden, The Netherlands). Mouse antibodies against human vascular cell adhesion molecule-1 (VCAM-1) (mIgG1), HLA-DR (mIgG2a), CD3 (mIgG1), CD40 (mIgG1), CD69 (mIgG1), MIG (mIgG1), MCP-1 (mIgG1), CD14 (mIgG1), IL-1α (mIgG1), P-selectin (mIgG1), DAF (mIgG2a), urokinase-type plasminogen activator receptor (uPAR) (mIgG1), and CD38 (mIgG1) were obtained from BD Biosciences (San Jose, Calif.). Mouse antibodies against eotaxin-3 (mIgG1), IL-8 (mIgG1), and M-CSF (mIgG1) were obtained from R&D Systems. Staphylococcal enterotoxin B, toxic shock syndrome toxin-1 (staphylococcal enterotoxin F) from *S. aureus* (collectively called superantigen; SAG), and lipopolysaccharide (LPS) from *Salmonella enteritidis* were obtained from Sigma.

Human umbilical vein endothelial cells (HUVEC) were cultured as described in Kunkel et al., 2004, *FASEB J* 18:1279-1281. Peripheral blood mononuclear cells (PBMC) were prepared from buffy coats (Stanford Blood Bank, Stanford, Calif.) by centrifugation over Hisopaque-1077 (Sigma). Four assay systems, 3C, 4H, SAG, and LPS, were used. For the 3C system, HUVEC were cultured for 24 h in microtiter plates (Falcon; BD Biosciences), in the presence of cytokines IL-1β (1 ng/ml), TNF-α (5 ng/ml), and IFN-γ (20 ng/ml). For the 4H system, HUVEC were cultured in the presence of IL-4 (5 ng/ml) and histamine (10 μM). For the SAG system, HUVEC were cultured with PBMC ($7.5 \times 10^4$) and SAG (20 ng/ml). For the LPS system, HUVEC were cultured with PBMC ($7.5 \times 10^4$) and LPS (2 ng/ml). Compounds were added 1 h before stimulation and were present during the entire 24-h stimulation period. Cell-based enzyme-linked immunosorbent assay (ELISAs) were carried out as described. (See Kunkel et al., 2004, *FASEB J* 18:1279-1281.)

Data Analysis

Mean optical density values for each parameter measured by ELISA were calculated from triplicate samples per experiment. Well-to-well coefficients of variance range from 1 to 12%, depending on the parameter measured, and average 5% across all controls. Day-to-day variability for a given readout, system, and treatment is the greatest contributor to the overall variability (ranging from 10 to 60% of the total variability), but is controlled for by using a prediction envelope to give the error boundaries for all the measurements simultaneously, consistent with our multivariate analysis approach. The envelope estimates the variability of the measurements around the mean (all data are centered). By combining similar measurements from multiple experiments, overall error measures are established while eliminating the specific bias of each experiment. Extensive studies have been performed concerning the number of repeats required for correctly classifying repeated profiles within given confidence limits leading to the requirement for at least three replicate wells per treatment and at least three independent repeats (unpublished observations).

Function Similarity Maps

Within each experiment, mean optical density values were used to generate ratios between treated (e.g., compound or siRNA) and matched control (e.g., media or dimethyl sulfoxide) parameter values. These normalized parameter ratios were then log 10 transformed. Log expression ratios were used in all Pearson correlation calculations. Correlations were visualized in two dimensions by multidimensional scaling using AT&T GraphViz software. Distances between compounds are representative of their similarities, and lines are drawn between compounds whose profiles are similar at a level not due to chance. Significant correlations were determined by (a) identifying the number of correlations that exceed a given threshold in the observed Pearson correlation distribution of the profiles, (b) calculating the average number of Pearson correlations that exceed this threshold using correlations calculated from randomized data made by permuting the empirical profiles multiple times, (c) reselecting the Pearson correlation threshold to minimize the false detection rate (FDR) (the FDR provides the probability that a significant correlation is a false positive), and (d) applying this cutoff Pearson correlation value to the correlations between experimental profiles. This ensures that for a 5% FDR, 95% of the correlations derived from the experimental profiles are not due to chance.

The results are presented in Table 1 below. Structure 13 in the Table is PP1 and not a compound of the invention. A "+" means that a compound was not active in the assay at a concentration of 5 micromolar. In one embodiment, the compounds of the invention are compounds other than compound nos. 1-57 in Table 1, below. In one embodiment, the methods of the invention are practiced with a compound shown in Table 1 other than PP1. In one embodiment, the methods of the invention are practiced with a compound in Table 1 that is identified as "active" in the Activity column. In one embodiment, the methods of the invention are practiced with a compound other than compound nos. 1-57 in Table 1, below.

TABLE 1

| No | Compound | Activity |
|---|---|---|
| 1. | [structure] | + |
| 2. | [structure] | + |
| 3. | [structure] | + |
| 4. | [structure] | + |
| 5. | [structure] | + |
| 6. | [structure] | active |
| 7. | [structure] | active |
| 8. | [structure] | active |

TABLE 1-continued

| No | Compound | Activity |
|---|---|---|
| 9. | 4-amino-3-(4-methylnaphthalen-1-yl)-1-tert-butyl-1H-pyrazolo[3,4-d]pyrimidine | active |
| 10. | 4-amino-3-(naphthalen-2-yl)-1-tert-butyl-1H-pyrazolo[3,4-d]pyrimidine | active |
| 11. | 4-amino-3-(acenaphthylen-5-yl)-1-tert-butyl-1H-pyrazolo[3,4-d]pyrimidine | active |
| 12. | 4-amino-3-(4-fluoronaphthalen-1-yl)-1-tert-butyl-1H-pyrazolo[3,4-d]pyrimidine | active |
| 13. | 4-amino-3-(p-tolyl)-1-tert-butyl-1H-pyrazolo[3,4-d]pyrimidine | active |
| 14. | 4-amino-3-(4-tert-butylphenyl)-1-tert-butyl-1H-pyrazolo[3,4-d]pyrimidine | + |
| 15. | 4-amino-3-(benzo[d][1,3]dioxol-5-yl)-1-tert-butyl-1H-pyrazolo[3,4-d]pyrimidine | active |
| 16. | 4-amino-3-(3-nitropyridin-2-yl)-1-tert-butyl-1H-pyrazolo[3,4-d]pyrimidine | + |

TABLE 1-continued
| No | Compound | Activity |
|---|---|---|
| 17. | 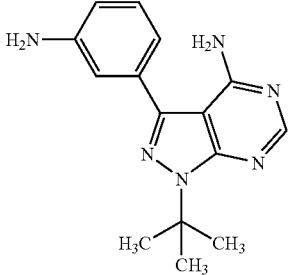 [SMILES: CC(C)(C)n1nc(-c2cccc(N)c2)c2c(N)ncnc21] | active |
| 18. | 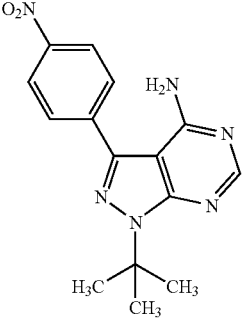 [SMILES: CC(C)(C)n1nc(-c2ccc([N+](=O)[O-])cc2)c2c(N)ncnc21] | + |
| 19. | 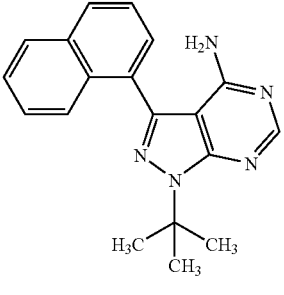 [SMILES: CC(C)(C)n1nc(-c2cccc3ccccc23)c2c(N)ncnc21] | active |
| 20. | 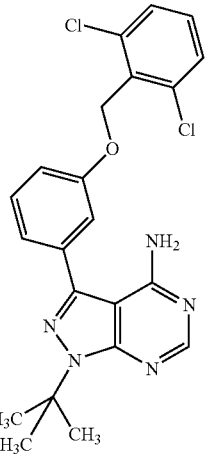 | + |
TABLE 1-continued
| No | Compound | Activity |
|---|---|---|
| 21. | 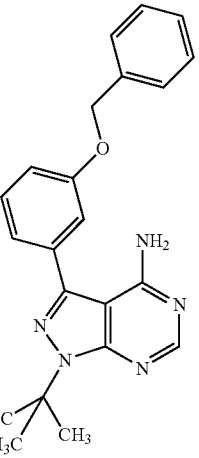 | + |
| 22. | 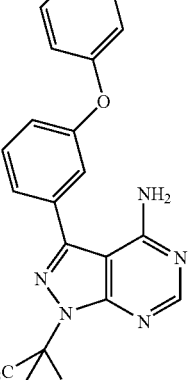 | active |
| 23. | 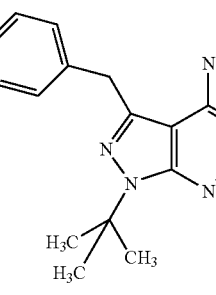 | + |
| 24. | 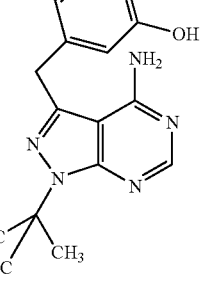 | + |

TABLE 1-continued

| No | Compound | Activity |
|---|---|---|
| 25. | 4-hydroxybenzyl-1-tert-butyl-1H-pyrazolo[3,4-d]pyrimidin-4-amine | + |
| 26. | 2-hydroxybenzyl-1-tert-butyl-1H-pyrazolo[3,4-d]pyrimidin-4-amine | + |
| 27. | 4-methoxybenzyl-1-tert-butyl-1H-pyrazolo[3,4-d]pyrimidin-4-amine | + |
| 28. | 2-methoxybenzyl-1-tert-butyl-1H-pyrazolo[3,4-d]pyrimidin-4-amine | + |
| 29. | 2-phenylethyl-1-tert-butyl-1H-pyrazolo[3,4-d]pyrimidin-4-amine | + |
| 30. | 2-chlorobenzyl-1-tert-butyl-1H-pyrazolo[3,4-d]pyrimidin-4-amine | active |
| 31. | 2-methylbenzyl-1-tert-butyl-1H-pyrazolo[3,4-d]pyrimidin-4-amine | active |
| 32. | 3-methylbenzyl-1-tert-butyl-1H-pyrazolo[3,4-d]pyrimidin-4-amine | + |
| 33. | 4-methylbenzyl-1-tert-butyl-1H-pyrazolo[3,4-d]pyrimidin-4-amine | + |

TABLE 1-continued

| No | Compound | Activity |
|----|----------|----------|
| 34. | (3-(1-phenylethyl)-1-tert-butyl-1H-pyrazolo[3,4-d]pyrimidin-4-amine) | + |
| 35. | (3-(cyclopentylmethyl)-1-tert-butyl-1H-pyrazolo[3,4-d]pyrimidin-4-amine) | + |
| 36. | (3-benzyl-1-tert-butyl-1H-pyrazolo[3,4-d]pyrimidin-4-amine) | active |
| 37. | (3-(2-chlorophenyl)-1-tert-butyl-1H-pyrazolo[3,4-d]pyrimidin-4-amine) | + |
| 38. | (3-cyclopentyl-1-tert-butyl-1H-pyrazolo[3,4-d]pyrimidin-4-amine) | + |
| 39. | (3-(m-tolyl)-1-tert-butyl-1H-pyrazolo[3,4-d]pyrimidin-4-amine) | active |
| 40. | (3-(2-(benzyloxy)phenyl)-1-tert-butyl-1H-pyrazolo[3,4-d]pyrimidin-4-amine) | + |
| 41. | (3-(3-hydroxyphenyl)-1-tert-butyl-1H-pyrazolo[3,4-d]pyrimidin-4-amine) | active |
| 42. | (methyl 2-(4-amino-3-(naphthalen-1-ylmethyl)-1H-pyrazolo[3,4-d]pyrimidin-1-yl)acetate) | + |
| 43. | (3-phenyl-1H-pyrazolo[3,4-d]pyrimidin-4-amine) | + |

TABLE 1-continued

| No | Compound | Activity |
|---|---|---|
| 44. | (3-isobutyl-1H-pyrazolo[3,4-d]pyrimidin-4-amine) | + |
| 45. | (3-benzyl-1H-pyrazolo[3,4-d]pyrimidin-4-amine) | + |
| 46. | (3-methyl-1H-pyrazolo[3,4-d]pyrimidin-4-amine) | + |
| 47. | (3-(naphthalen-2-yl)-1H-pyrazolo[3,4-d]pyrimidin-4-amine) | active |
| 48. | (1-methyl-3-(naphthalen-2-yl)-1H-pyrazolo[3,4-d]pyrimidin-4-amine) | active |
| 49. | (1,3-diphenyl-1H-pyrazolo[3,4-d]pyrimidin-4-amine) | + |
| 50. | (3-(4-amino-7-isopropyl-7H-pyrrolo[2,3-d]pyrimidin-5-yl)phenol) | active |
| 51. | (1-(2-methoxyethyl)-3-phenyl-1H-pyrazolo[3,4-d]pyrimidin-4-amine) | + |
| 52. | (3-(4-amino-1-(2-methoxyethyl)-1H-pyrazolo[3,4-d]pyrimidin-3-yl)phenol) | active |
| 53. | (3-(4-(benzylamino)-7-isopropyl-7H-pyrrolo[2,3-d]pyrimidin-5-yl)phenol) | active |
| 54. | (3-(4-amino-1-isopropyl-1H-pyrazolo[3,4-d]pyrimidin-3-yl)phenol) | active |

TABLE 1-continued

| No | Compound | Activity |
|---|---|---|
| 55. | 3-hydroxyphenyl-7-isopropyl-N-methyl-7H-pyrrolo[2,3-d]pyrimidin-4-amine | + |
| 56. | 3-(3-aminophenyl)-1-isopropyl-N-methyl-1H-pyrazolo[3,4-d]pyrimidin-4-amine | + |
| 57. | 1-benzyl-4-chloro-3-phenyl-1H-pyrazolo[3,4-d]pyrimidine | + |
| 58. | 3-(2-bromobenzyl)-1-methyl-1H-pyrazolo[3,4-d]pyrimidin-4-amine | + |
| 59. | 3-(2-bromobenzyl)-1-tert-butyl-1H-pyrazolo[3,4-d]pyrimidin-4-amine | active |
| 60. | 1-tert-butyl-3-(2,6-dichlorobenzyl)-1H-pyrazolo[3,4-d]pyrimidin-4-amine | active |
| 61. | 3-(2-chlorobenzyl)-1-methyl-1H-pyrazolo[3,4-d]pyrimidin-4-amine | + |
| 62. | 3-(2-chlorobenzyl)-1-isopropyl-1H-pyrazolo[3,4-d]pyrimidin-4-amine | active |
| 63. | 3-(2-chlorobenzyl)-1-cyclopentyl-1H-pyrazolo[3,4-d]pyrimidin-4-amine | active |
| 64. | 1-tert-butyl-3-(2-fluorobenzyl)-1H-pyrazolo[3,4-d]pyrimidin-4-amine | active |

TABLE 1-continued

| No | Compound | Activity |
|---|---|---|
| 65. | (structure: 4-amino-1-tert-butyl-3-(2-(trifluoromethyl)benzyl)-1H-pyrazolo[3,4-d]pyrimidine) | active |
| 66. | (structure: 4-amino-3-((2-methylthiophen-3-yl)methyl)-1H-pyrazolo[3,4-d]pyrimidine) | active |
| 67. | (structure: 4-amino-1-tert-butyl-3-((2-methylthiophen-3-yl)methyl)-1H-pyrazolo[3,4-d]pyrimidine) | active |
| 68. | (structure: 4-amino-1-tert-butyl-3-(2,4-dichlorobenzyl)-1H-pyrazolo[3,4-d]pyrimidine) | + |
| 69. | (structure: 4-amino-1-tert-butyl-3-(2-chloro-4-fluorobenzyl)-1H-pyrazolo[3,4-d]pyrimidine) | + |
| 70. | (structure: 4-amino-3-(2-chlorobenzyl)-1-(2-ethoxyethyl)-1H-pyrazolo[3,4-d]pyrimidine) | + |
| 71. | (structure: 4-amino-3-(2-chlorobenzyl)-1-methyl-1H-pyrazolo[3,4-d]pyrimidine) | + |
| 72. | (structure: 4-amino-3-(2-chlorobenzyl)-1-neopentyl-1H-pyrazolo[3,4-d]pyrimidine) | active |
| 73. | (structure: methyl 4-(4-amino-3-(2-chlorobenzyl)-1H-pyrazolo[3,4-d]pyrimidin-1-yl)butanoate) | + |
| 74. | (structure: 4-(4-amino-3-(2-chlorobenzyl)-1H-pyrazolo[3,4-d]pyrimidin-1-yl)butan-1-ol) | + |

TABLE 1-continued

| No | Compound | Activity |
|---|---|---|
| 75. | | + |
| 76. | | active |
| 77. | | active |
| 78. | | active |
| 79. | | active |
| 80. | | active |
| 81. | | active |
| 82. | | active |
| 83. | | active |
| 84. | | active |

TABLE 1-continued

| No | Compound | Activity |
|---|---|---|
| 85. | 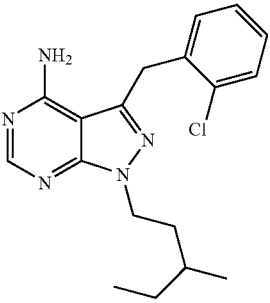 [SMILES: CCC(C)CCn1nc(Cc2ccccc2Cl)c2c(N)ncnc21] | active |
| 86. | 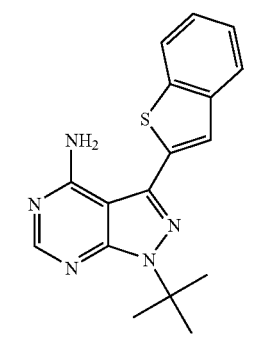 [SMILES: CC(C)(C)n1nc(-c2cc3ccccc3s2)c2c(N)ncnc21] | active |
| 87. | 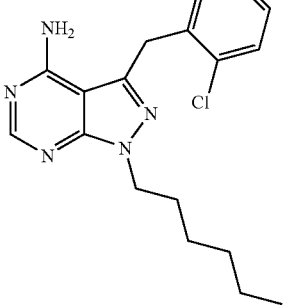 | active |
| 88. | 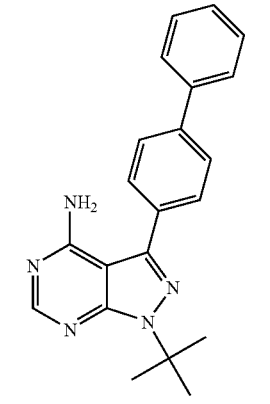 [SMILES: CC(C)(C)n1nc(-c2ccc(-c3ccccc3)cc2)c2c(N)ncnc21] | active |

TABLE 1-continued

| No | Compound | Activity |
|---|---|---|
| 89. | 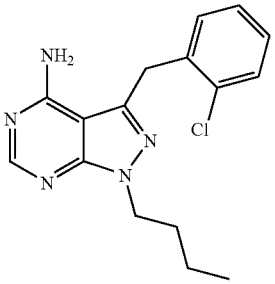 [SMILES: CCCCn1nc(Cc2ccccc2Cl)c2c(N)ncnc21] | active |

In Table 1, the term "active" indicates that at least 3 parameters (in the 4 systems tested (3C, 4H, SAG, and LPS)) simultaneously showed activity falling outside a 99% prediction envelope, as described above.

Table 2, below, shows certain compounds that did not exhibit activity in the systems tested at a concentration of 10 micromolar. In one embodiment, the compounds of the invention are compounds other than the compounds shown in Table 2. In one embodiment, the methods of the invention are practiced with a compound other than a compound shown in Table 2, below.

TABLE 2

| No | Compound |
|---|---|
| 1. | 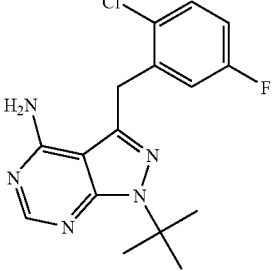 |
| 2. | 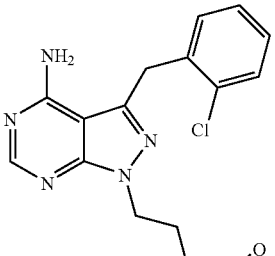 |
| 3. | 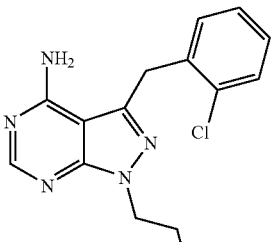 |

TABLE 2-continued

| No | Compound |
|---|---|
| 4. | (structure: 4-amino pyrazolo[3,4-d]pyrimidine with 2-chlorobenzyl at 3-position and 2,2-dimethyl-3-hydroxypropyl at N1) |
| 5. | (structure: 4-hydroxy pyrazolo[3,4-d]pyrimidine with 2-chlorobenzyl at 3-position and tert-butyl at N1) |
| 6. | (structure: 4-amino pyrazolo[3,4-d]pyrimidine with 2-chlorobenzyl at 3-position and ethyl at N1) |

Example 2

The following compounds provide illustrative characterization data for certain pyrazolopyrimidine compounds. All starting materials and synthetic reagents were purchased from commercial suppliers unless otherwise noted. Acid chlorides that were not readily commercially available were synthesized by treating the corresponding carboxylic acids with excess oxalyl chloride and catalytic DMF in diethyl ether, as described in Ward and Rhee, 1991, *Tetrahedron Lett.* 32:7165-7166. Useful protocols were adapted from Hanefeld et al. 1996, *J. Chem. Soc., Perkin Trans.* 1, 1996, 1545-1552. One skilled in the art will immediately recognize that any differences in naming convention is not intended to limit the illustrative value of the examples disclosed herein.

1-tert-Butyl-3-(2,5-dimethylbenzyl)-1H-pyrazolo[3,4-d]pyrimidin-4-ylamine

White powder; $^1$H NMR (CDCl$_3$, 400 MHz) δ 1.79 (s, 9H), 2.20 (s, 3H), 2.25 (s, 3H), 4.22 (s, 2H), 4.94 (s, 2H), 6.81 (s, 1H), 6.98 (d, 1H), 7.08 (d, 1H), 8.23 (s, 1H); $^{13}$C NMR (CDCl$_3$, 100 MHz) δ 19.3, 21.0, 29.2, 33.1, 59.9, 100.9, 128.1, 129.1, 130.9, 133.6, 135.9, 136.3, 140.9, 154.3, 154.6, 157.7; HRMS (EI) molecular ion calculated for C$_{18}$H$_{23}$N$_5$, 309.19535. found 309.19386.

1-tert-Butyl-3-(3,5-dimethylbenzyl)-1H-pyrazolo[3,4-d]pyrimidin-4-ylamine

White powder; $^1$H NMR (CDCl$_3$, 400 MHz) δ 1.80 (s, 9H), 2.25 (s, 6H), 4.20 (s, 2H), 5.00 (s, 2H), 6.80 (s, 2H), 6.88 (s, 1H), 8.22 (s, 1H); $^{13}$C NMR (CDCl$_3$, 100 MHz) δ 21.3, 29.2, 35.1, 59.9, 100.7, 126.2, 129.0, 138.0, 138.9, 141.3, 154.4, 154.7, 157.7; HRMS (EI) molecular ion calculated for C$_{18}$H$_{23}$N$_5$, 309.19535. found 309.19439.

1-tert-Butyl-3-(3,4-dichlorobenzyl)-1H-pyrazolo[3,4-d]pyrimidin-4-ylamine

White powder; $^1$H NMR (CDCl$_3$, 400 MHz) δ 1.79 (s, 9H), 4.24 (s, 2H), 5.07 (s, 2H), 7.02 (dd, 1H), 7.29 (d, 1H), 7.37 (d, 1H), 8.26 (s, 1H); $^{13}$C NMR (CDCl$_3$, 100 MHz) δ 29.1, 34.3, 60.2, 100.6, 127.6, 130.2, 131.0, 131.4, 133.2, 138.4, 139.2, 154.6, 154.7, 157.5; HRMS (EI) molecular ion calculated for C$_{16}$H$_{17}$N$_5$Cl$_2$, 349.08610. found 349.08621.

1-tert-Butyl-3-(4-chlorobenzyl)-1H-pyrazolo[3,4-d]pyrimidin-4-ylamine

White powder; $^1$H NMR (CDCl$_3$, 400 MHz) δ 1.77 (s, 9H), 4.25 (s, 2H), 5.16 (br s, 2H), 7.11 (d, J=8 Hz, 2H), 7.27 (d, J=8 Hz, 2H), 8.22 (s, 1H); $^{13}$C NMR (CDCl$_3$, 100 MHz) δ 29.1, 34.5, 60.0, 100.6, 129.3, 129.6, 133.1, 136.6, 140.1, 154.5, 154.6, 157.6; HRMS (EI) molecular ion calculated for C$_{16}$H$_{18}$N$_5$Cl, 315.12507. found 315.12545.

1-tert-Butyl-3-(4-methoxybenzyl)-1H-pyrazolo[3,4-d]pyrimidin-4-ylamine

White powder; $^1$H NMR (CDCl$_3$, 400 MHz) δ 1.78 (s, 9H), 3.76 (s, 3H), 4.22 (s, 2H), 4.91 (br s, 2H), 6.84 (d, J=9 Hz, 2H), 7.11 (d, J=9 Hz, 2H), 8.22 (s, 1H); $^{13}$C NMR (CDCl$_3$, 100 MHz) δ 29.2, 34.3, 55.2, 59.9, 100.6, 114.6, 129.4, 130.0, 141.4, 154.5, 154.7, 157.6, 158.7; HRMS (EI) molecular ion calculated for C$_{17}$H$_{21}$N$_5$O, 311.17461. found 311.17454.

1-tert-Butyl-3-(2-methoxybenzyl)-1H-pyrazolo[3,4-d]pyrimidin-4-ylamine

White powder; $^1$H NMR (CDCl$_3$, 400 MHz) δ 1.77 (s, 9H), 3.89 (s, 3H), 4.25 (s, 2H), 5.77 (br s, 2H), 6.89 (m, 2H), 7.18 (m, 2H), 8.20 (s, 1H); $^{13}$C NMR (CDCl$_3$, 100 MHz) δ 27.4, 29.2, 55.5, 59.8, 100.4, 110.8, 121.5, 126.5, 128.0, 130.6, 141.1, 154.3, 154.3, 155.7, 158.0; HRMS.

1-tert-Butyl-3-(2-chlorobenzyl)-1H-pyrazolo[3,4-d]pyrimidin-4-ylamine

White powder; $^1$H NMR (CDCl$_3$, 400 MHz) δ 1.78 (s, 9H), 4.38 (s, 2H), 5.41 (br s, 2H), 7.00 (dd, J$_1$=7 Hz, J$_2$=2 Hz, 1H), 7.15 (m, 2H), 7.39 (dd, J$_1$=8 Hz, J$_2$=2 Hz, 1H), 8.22 (s, 1H); $^{13}$C NMR (CDCl$_3$, 100 MHz) δ 29.1, 31.9, 60.0, 100.7, 127.4, 128.4, 129.6, 130.1, 133.3, 135.6, 139.4, 154.4, 154.5, 157.7; HRMS (EI) molecular ion calculated for C$_{16}$H$_{18}$N$_5$Cl, 315.12507. found 315.12449.

1-tert-Butyl-3-(2-methylbenzyl)-1H-pyrazolo[3,4-d]pyrimidin-4-ylamine

White powder; $^1$H NMR (CDCl$_3$, 400 MHz) δ 1.77 (s, 9H), 2.30 (s, 3H), 4.25 (s, 2H), 5.09 (br s, 2H), 6.98 (d, J=8

Hz, 1H), 7.14 (m, 3H), 8.20 (s, 1H); $^{13}$C NMR (CDCl$_3$, 100 MHz) δ 19.8, 29.1, 33.1, 59.9, 100.9, 126.7, 127.3, 128.3, 130.8, 136.1, 136.8, 140.6, 154.3, 154.5, 157.8; HRMS (EI) molecular ion calculated for C$_{17}$H$_{21}$N$_5$, 295.17970. found 295.17922.

1-tert-Butyl-3-(4-methylbenzyl)-1H-pyrazolo[3,4-d]pyrimidin-4-ylamine

White powder; $^1$H NMR (CDCl$_3$, 400 MHz) δ 1.79 (s, 9H), 2.30 (s, 3H), 4.24 (s, 2H), 4.94 (br s, 2H), 7.08 (d, J=8 Hz, 2H), 7.11 (d, J=8 Hz, 2H), 8.21 (s, 1H); $^{13}$C NMR (CDCl$_3$, 100 MHz) δ 21.0, 29.2, 34.8, 59.9, 100.6, 128.3, 130.0, 135.1, 136.9, 141.3, 154.5, 154.7, 157.7; HRMS (EI) molecular ion calculated for C$_{17}$H$_{21}$N$_5$, 295.17970. found 295.18068.

1-tert-Butyl-3-cyclopentylmethyl-1H-pyrazolo[3,4-d]pyrimidin-4-ylamine

White powder; $^1$H NMR (CDCl$_3$, 400 MHz) δ 1.28 (m, 2H), 1.53 (m, 2H), 1.65 (m, 2H), 1.71 (m, 2H), 1.73 (s, 9H), 2.28 (m, 1H), 2.86 (d, J=8 Hz, 2H), 5.69 (br s, 2H), 8.25 (s, 1H); $^{13}$C NMR (CDCl$_3$, 100 MHz) δ 25.0, 29.2, 32.4, 35.2, 39.7, 59.7, 100.5, 142.1, 153.0, 154.0, 158.0; HRMS (EI) molecular ion calculated for C$_{15}$H$_{23}$N$_5$, 273.19535. found 273.19565.

4-Amino-1-tert-butyl-3-(1'-naphthyl)pyrazolo[3,4-d]pyrimidine white powder; $^1$H NMR (270 MHz, CDCl$_3$) δ 1.92 (s, 9H), 5.04 (m, 2H), 7.43-7.73 (m, 4H), 7.92-8.02 (m, 3H), 8.34 (s, 1H); HRMS (EI) molecular ion calculated for C$_{19}$H$_{19}$N$_5$, 317.16427. found 317.16247.

4-Amino-1-tert-butyl-3-(2'-naphthyl)pyrazolo[3,4-d]pyrimidine white powder; $^1$H NMR (270 MHz, CDCl$_3$) δ 1.88 (s, 9H), 5.55 (m, 2H), 7.56-8.00 (m, 6H), 8.16 (s, 1H), 8.39 (s, 1H); HRMS (EI) molecular ion calculated for C$_{19}$H$_{19}$N$_5$, 317.16427. found 317.16359.

4-Amino-1-tert-butyl-3-(m-phenoxyphenyl)pyrazolo[3,4-d]pyrimidine white powder; $^1$H NMR (270 MHz, CDCl$_3$) δ 1.83 (s, 9H), 5.61 (s, 2H), 7.08-7.49 (m, 9H), 8.35 (s, 1H); HRMS (EI) molecular ion calculated for C$_{21}$H$_{21}$N$_5$O, 359.17483. found 359.17325.

4-Amino-1-tert-butyl-3-(m-benzyloxyphenyl)pyrazolo[3,4-d]pyrimidine white powder; $^1$H NMR (270 MHz, CDCl$_3$) δ 1.85 (s, 9H), 5.17 (s, 2H), 5.55 (s, 2H), 7.10 (d, J) 8 Hz, 1H), 7.27-7.48 (m, 8H), 8.34 (s, 1H); HRMS (EI) molecular ion calculated for C$_{22}$H$_{23}$N$_5$O, 373.19049. found 373.18833.

4-Amino-1-tert-butyl-3-(m-(2',6'-dichloro)benzyloxyphenyl)pyrazolo[3,4-d]pyrimidine white powder; $^1$H NMR (270 MHz, CDCl$_3$) δ 1.85 (s, 9H), 5.36 (s, 2H), 5.74 (s, 2H), 7.11-7.51 (m, 7H), 8.36 (s, 1H); HRMS (EI) molecular ion calculated for C$_{22}$H$_{21}$Cl$_2$N$_5$O, 441.11263. found 441.11050.

4-Amino-1-tert-butyl-3-piperonylpyrazolo[3,4-d]pyrimidine white powder; $^1$H NMR (270 MHz, CDCl$_3$) δ 1.83 (s, 9H), 5.70 (s, 2H), 6.05 (s, 2H), 6.96 (d, J) 8 Hz, 1H), 7.13-7.27 (m, 2H), 8.34 (s, 1H); HRMS (EI) molecular ion calculated for C$_{16}$H$_{17}$N$_5$O$_2$, 311.13841. found 311.13777.

4-Amino-1-tert-butyl-3-(p-tert-butylphenyl)pyrazolo[3,4-d]pyrimidine white powder; $^1$H NMR (300 MHz, CDCl$_3$) δ 1.38 (s, 9H), 1.84 (s, 9H), 5.83 (s, 2H), 7.58 (dd, J) 8 Hz, 12 Hz, 4H), 8.33 (s, 1H); HRMS (EI) molecular ion calculated for C$_{19}$H$_{25}$N$_5$, 323.21125. found 323.21024.

4-Amino-1-tert-butyl-3-(1'-naphthylmethyl)pyrazolo[3,4-d]pyrimidine white powder; $^1$H NMR (270 MHz, CDCl$_3$) δ 1.85 (s, 9H), 4.76 (s, 2H), 5.04 (s, 2H), 7.19 (d, J) 6 Hz, 1H), 7.39 (t, J) 8 Hz, 1H), 7.55 (t, J) 4 Hz, 2H), 7.79-7.92 (m, 2H), 8.20 (d, J) 8 Hz, 1H), 8.24 (s, 1H); HRMS (EI) molecular ion calculated for C$_{20}$H$_{21}$N$_5$, 331.17993. found 331.17951.

4-Amino-1-tert-butyl-3-(1'-naphthoxymethyl)pyrazolo[3,4-d]pyrimidine beige powder; $^1$H NMR (270 MHz, CDCl$_3$) δ 1.83 (s, 9H), 5.57 (s, 2H), 6.12 (s, 2H), 7.07 (d, J) 7 Hz, 1H), 7.39-7.54 (m, 4H), 7.84 (d, J) 8 Hz, 1H), 8.25 (d, J) 8 Hz, 1H), 8.35 (s, 1H); HRMS (EI) molecular ion calculated for C$_{20}$H$_{21}$N$_5$O, 347.17483. found 347.17408.

Example 3

The following example illustrates the ability of a compound useful in the methods of the present invention to reduce neutrophil and monocyte recruitment, as well as to reduce the total number of leukocytes in a mouse peritoneal inflammation model.

A single dose (10 mg/kg in 200 μl) of an anti-inflammatory pyrazolopyrimidine compound of the present invention (compound 30 in Table 1, above) was administered intraperionteally to a group of 6 mice while another group of 6 mice received an intraperitoneal injection of vehicle only. Fifteen minutes later, an inflammatory stimulus (thioglycollate, 200 μl) was administered intraperitoneally to each mouse. Peritoneal lavage was collected at 4 and 24 hours subsequent to stimulus administration.

Inflammatory infiltrate was recovered by injection of 10 ml of Ca++/Mg++ free PBS, massaging, and withdrawal. Total recovered cells were counted on a hemacytometer. The results are presented in FIG. 2 (average+/−SD of 6 mice).

Figure 3:
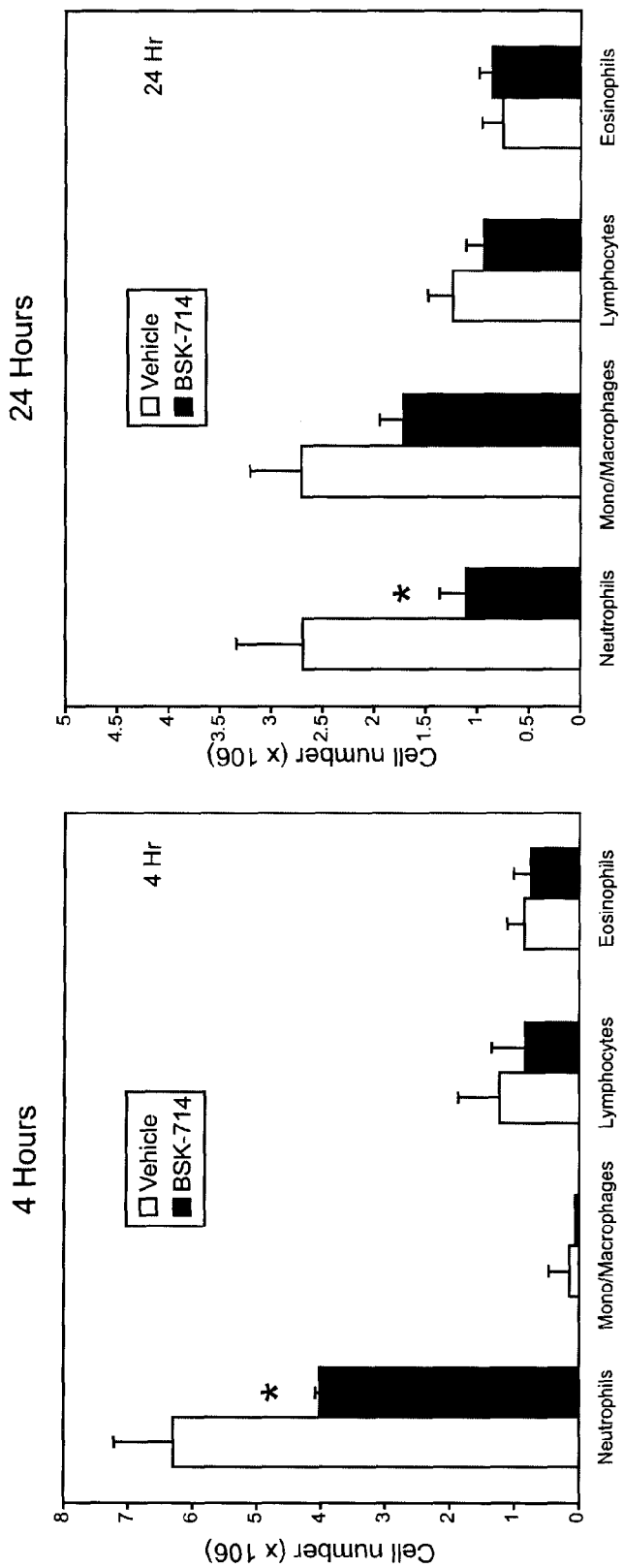
FIG. 3 illustrates the decrease in macrophage and neutrophil recruitment in a mouse model of peritoneal inflammation resulting from the administration of an anti-inflammatory pyrazolopyrimidine of the present invention.

Neutrophils, monocytes, lymphocytes and eosinophils were enumerated by analyzing smears of the peritoneal wash stained with Wright-Geimsa stain. The results are presented in FIG. 3 (average+/−SD of 6 mice).

What is claimed is:

1. A compound having the formula:

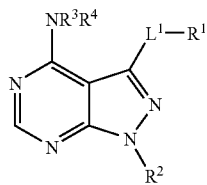

wherein
- $R^1$ is $R^{15}$-substituted or unsubstituted fused ring heteroaryl;
- $R^2$, $R^3$, and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted aryl, or substituted or unsubstituted heteroaryl;
- $R^{15}$ is —OH, halogen, —CF$_3$, —NH$_2$, substituted or unsubstituted heteroalkyl, substituted or unsubstituted cycloalkyl, or substituted or unsubstituted heterocycloalkyl;
and
- $L^1$ is a bond or unsubstituted alkylene.

2. A compound according to claim 1, wherein $R^2$ is $R^{10}$-substituted $C_1$-$C_{20}$ alkyl, 2 to 20 membered substituted or unsubstituted heteroalkyl, $R^{11}$-substituted $C_3$-$C_8$ cycloalkyl, $R^{11}$-substituted $C_3$-$C_8$ heterocycloalkyl, $R^{12}$-substituted heteroaryl, or $R^{13}$-substituted aryl, wherein $R^{10}$ is oxo, —OH, halogen, —CF$_3$, —NH$_2$, 2 to 20 membered substituted or unsubstituted heteroalkyl, 3 to 7 membered substituted or unsubstituted heterocycloalkyl, substituted or unsubstituted heteroaryl, or $R^{13}$-substituted aryl, $R^{11}$ is oxo, —OH, halogen, —CF$_3$, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^{12}$ is —OH, halogen, —CF$_3$, —NH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, and $R^{13}$ is —OH, —NH$_2$, substituted or unsubstituted cycloalkyl, substituted or unsubstituted heterocycloalkyl, substituted or unsubstituted heteroaryl, or substituted or unsubstituted aryl.

3. The compound of claim 1, wherein $R^3$ and $R^4$ are hydrogen.

4. The compound of claim 1, wherein $R^1$ is a fused-ring heteroaryl substituted with one $R^{15}$ substituent.

5. The compound of claim 4, wherein $R^{15}$ is —OH, halogen, —CF$_3$, or —NH$_2$.

6. The compound of claim 1, wherein $R^2$ is substituted or unsubstituted alkyl.

* * * * *